United States Patent [19]

Chu

[11] Patent Number: 5,455,339
[45] Date of Patent: * Oct. 3, 1995

[54] METHOD FOR THE PREPARATION OF 2',3'-DIDEOXY AND 2',3'-DIDEOXYDIDE-HYDRO NUCLEOSIDES

[75] Inventor: Chung K. Chu, Athens, Ga.

[73] Assignee: University of Georgia Research Foundation, Inc., Athens, Ga.

[*] Notice: The portion of the term of this patent subsequent to Jan. 24, 2012 has been disclaimed.

[21] Appl. No.: 966,580

[22] Filed: Oct. 26, 1992

Related U.S. Application Data

[63] Continuation of Ser. No. 318,694, Mar. 3, 1989, abandoned, which is a continuation-in-part of Ser. No. 159,246, Feb. 23, 1988, abandoned, which is a continuation-in-part of Ser. No. 16,136, Feb. 18, 1987, Pat. No. 4,841,039, which is a continuation of Ser. No. 857,947, May 1, 1986, Pat. No. 4,681,933, and Ser. No. 104,438, Oct. 2, 1987, Pat. No. 4,916,122, which is a continuation-in-part of Ser. No. 7,473, Jan. 28, 1987, abandoned.

[51] Int. Cl.$^6$ .................................................. C07H 19/00
[52] U.S. Cl. .................. 536/27.14; 536/28.53; 536/28.8; 536/28.5; 536/28.52
[58] Field of Search .................. 536/27.14, 28.53, 536/28.8, 26.8, 28.5, 28.52

[56] References Cited

U.S. PATENT DOCUMENTS

| | | | |
|---|---|---|---|
| 3,282,921 | 11/1966 | Verheyden et al. | 536/28.2 |
| 3,687,931 | 8/1972 | Verheyden et al. | 536/27.14 |
| 3,755,295 | 8/1973 | Verheyden et al. | 536/28.55 |
| 3,775,397 | 11/1973 | Etzold et al. | 536/28.2 |
| 3,817,982 | 6/1974 | Verheyden et al. | 536/28.53 |
| 4,071,680 | 1/1978 | Cook | 536/28.52 |
| 4,230,698 | 10/1980 | Bobek et al. | 514/49 |
| 4,604,382 | 8/1989 | Lin et al. | 514/49 |
| 4,788,101 | 11/1989 | Driscoll et al. | 514/49 |
| 4,904,770 | 2/1990 | Starrett, Jr. et al. | 536/27.14 |
| 4,921,950 | 5/1990 | Wilson | 536/28.54 |

FOREIGN PATENT DOCUMENTS

| | | |
|---|---|---|
| 86301897 | 10/1986 | European Pat. Off. . |
| 86307071 | 4/1987 | European Pat. Off. . |
| 0292101 | 11/1988 | European Pat. Off. . |
| 1068578 | 10/1974 | Japan ........... 536/23 |
| 8523878 | 9/1985 | United Kingdom . |
| 8603447 | 1/1986 | United Kingdom . |

OTHER PUBLICATIONS

Anzai, et al., *Agri. Biol. Chem.* 37(2), 345 (1973).
Barrett, et al., *J.C.S. Chem. Comm.* 866 (1977).
Barrett, et al., *J.C.S. Perkin I* 2378 (1979).
Classon, et al., *Acta Chemica Scandinavica* B36, 251 (1982).
Colla, et al., *Eur. J. Med. Chem. — Chim. Ther.* 20(4), 295 (1985).
Chem. Abstract 101:192378c (1984).
Chem. Abstract 96:69346s (1982).
Chem. Abstract 105:227205f (1986).
Dyatkina, *Sovie J. Biorg. Chem.* 12, 563 (1986).
Herdewijn, et al., *J. Med. Chem.* 30, 1270 (1987).
Horton, et al., *J. Org. Chem.* 35, 10 (1970).
Horowitz, et al., *J. Am. Chem. Soc.* 86, 1896 (1964).
Horowitz, et al., *J. Org. Chem.* 29, 2076 (1984).
Horowitz, et al., *J. Org. Chem.* 31, 205 (1966).
Horowitz, et al., *J. Org. Chem.* 32, 817 (1967).
Horowitz, et al., *Tet. Letters* 1343 (1966).
Jain, et al., *J. Org. Chem.* 39, 30 (1974).
Lin, et al., *Biochem. Pharmacol.* 36, 2713 (1987).
Lin, et al., *J. Med. Chem.* 30, 440 (1987).
Lin, et al., *J. Med. Chem.* 21(1), 109 (1978).
Lin, et al., *J. Med. Chem.* 26, 1691 (1983).
Lin, et al., *J. Med. Chem.* 26, 544 (1983).
Krenitsky, et al, *J. Med. Chem.* 26(6), 891 (1983).
McCarthy, et al., *J. Am. Chem. Soc.* 88, 1549 (1966).
Prisbe and Martin, *Synthec Communications* 15(5), 401, (1985).
Robins, et al., *Tet. Letters* 25, 367 (1984).
Russell, et al., *J. Am. Chem. Soc.* 95, 4025 (1973).
Tong, et al., *J. Org. Chem.* 30, 2854 (1965).
Webb, et al., *Nucleosides and Nucleotides* 7(2), 147 (1988).
*Agr. Biol. Chem.*, 37(2), p. 345–348 (1973).

*Primary Examiner*—Che S. Chereskin
*Attorney, Agent, or Firm*—Cheryl K. Zalesky; Kilpatrick & Cody

[57] ABSTRACT

A method for preparing 2',3'-didehydrodideoxynucleosides and the corresponding reduced 2',3'-dideoxynucleosides which includes i) preparing a nucleoside derivative of the general structure

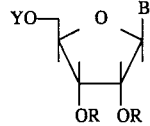

wherein B is a nitrogen, oxygen, or sulfur heterocycle of from $C_1$ to $C_{15}$, Y is a suitable oxygen protecting group, each R is $C(S)SR'$, where R' is an alkyl or cyanoalkyl group of $C_1$ to $C_{15}$, or both Rs together are $>C=S$: and then ii) deoxygenating the nucleoside derivative to the corresponding 2',3'-didehydrodideoxynucleoside.

28 Claims, 6 Drawing Sheets

1

2

3

4

5

6

7 X = $NH_2$, Y = H
8 X = OH, Y = H
9 X = OH, Y = $NH_2$

10 X = $NH_2$, Y = H
11 X = OH, Y = H
12 X = OH, Y = $NH_2$ i) t-BDMSi-Cl/Imidazole; $CS_2$/NaOH, $CH_3I$;

ii) t-BDMSi-Cl/Imidazole; Thiocarbonyl diimidazole;

iii) $Bu_3SnH$/AIBN;

iv) $(EtO)_3P$ or 1,3-dimethyl-2-phenyl 1,3,2-diazaphosphilidine; v) $Bu_4NF$; vi) $H_2$, Pd/C.

i) t-BDMSi-Cl/Imidazole; ii) CS$_2$/NaOH, BrCH$_2$CH$_2$CN;
iii) Thiocarbonyl diimidazole; iv) Bu$_3$SnH/AIBN;
v) (EtO)$_3$P; vi) Bu$_4$NF; vii) H$_2$, Pd/C i) $Ac_2O$/MeOH; t-BDMSiCl/Imidazole; NaH /$CS_2$,$CH_3$I;
ii) t-BDMSi-Cl/Imidazole; Thiocarbonyl diimidazole;
iii) $Bu_3SnH$/AIBN; iv) $Bu_4NF$; v) $H_2$, Pd/C; vi) $NH_3$/MeOH.

i) t-BDMSiCl/Imidazole; CS$_2$/NaOH, CH$_3$I; ii) Bu$_3$SnH/AIBN
iii) Bu$_4$NF; iv) t-BDMSiCl/Imidazole; CS$_2$/NaOH, BrCH$_2$CH$_2$CN
v) t-BDMSi-Cl/Imidazole; Thiocarbonyl diimidazole;
vi) (EtO)$_3$P or 1,3-dimethy-2-phenyl-1,3,2-diazapholidine

METHOD FOR THE PREPARATION OF 2',3'-DIDEOXY AND 2',3'-DIDEOXYDIDE-HYDRO NUCLEOSIDES

This is a continuation of copending application Ser. No. 07/318,694 filed on Mar. 3, 1989, now abandoned, which is a Continuation-in-Part of U.S. Ser. No. 159,246 entitled "2',3'-Dideoxynucleosides as Anti-Retroviral Compositions and Their Method of Preparation", filed Feb. 23, 1988, now abandoned, which is a Continuation-in-Part of (1) U.S. patent application Ser. No. 016,136 entitled "2',3'-Dideoxy-5-Substituted Uridines and Related Compounds as Antiviral Agents" filed Feb. 18, 1987 by Chung K. Chu and Raymond F. Schinazi, now U.S. Pat. No. 4,841,039, which is a continuation of U.S. Ser. No. 857,947 filed May 1, 1986 by Chung K. Chu and Raymond F. Schinazi, now U.S. Pat. No. 4,681,933, and (2) U.S. patent application Ser. No. 104,438 filed Oct. 2, 1987 entitled "3'-Azido- 2',3'-Dideoxyuridine Antiviral Composition" by Chung K. Chu and Raymond F. Schinazi, now U.S. Pat. No. 4,916,122 which is a continuation in part of U.S. Ser. No. 007,473 filed Jan. 28, 1987 entitled "3'-Azido-2',3'-Dideoxypyrimidines and Related Compounds as Antiviral Agents", now abandoned.

BACKGROUND OF THE INVENTION

The present invention is in the area of biochemistry, and is in particular a method of preparation of 2',3'-dideoxy and 2',3'-dideoxydidehydro nucleosides.

Since 3'-azido-3'-deoxythymidine (FIG. 1, Compound 1) (AZT, Zidovudine, Retrovir) was identified by Mitsuya et al. as a potent antiviral agent against human immunodeficiency virus type 1 (HIV-1), alternatively called human T-lymphotropic virus type III (HTLV-III), a number of other nucleosides have been found to inhibit HIV-1 in vitro.

In particular, a number of 2',3'-dideoxy and 2',3'-didehydrodideoxy nucleosides have been shown to have potent anti-HIV-1 activity. Examples of 2',3'-dideoxy nucleosides which exhibit antiviral activity include 2',3'-dideoxycytidine (DDC), 2',3'-dideoxyadenosine (DDA), 3'-azido-2',3'-dideoxyuridine (CS-87), 2',3'-dideoxyuridine, 2',3'-dideoxyinosine, 2',3'-dideoxyguanosine, 3'-azido-methyl-2',3'-dideoxycytidine (CS-92), and 3'-azido-2',3'-dideoxyuridine (CS-85). Examples of 2',3'-didehydrodideoxy nucleosides (2',3'-unsaturated nucleosides) with antiviral activity include 2',3'-didehydrodideoxycytidine, 2',3'-didehydrodideoxyuridine, 2',3'-didehydrodideoxyadenosine, 2',3'-dideoxydidehydroinosine, and 2',3'-dideoxydidehydroguanosine.

In view of the importance of 2',3'-dideoxynucleosides and 2',3'-dideoxydidehydro nucleosides, it is desirable to have a facile, efficient and general route of synthesis to these compounds. While several methods exist for the synthesis of 2',3'-dideoxynucleosides and 2',3'-didehydrodideoxy nucleosides, none has the ability to produce both types of nucleosides in an easy procedure which is applicable to both purine and pyrimidine nucleosides.

The first reported method to produce 2',3'-didehydrodideoxy nucleosides involved the base promoted elimination of 3'-O-sulfonyl esters of 2'-deoxyynucleosides. However, the synthetic route is limited to pyrimidines and cannot be used for purines. Horowitz, J. P., ea al., *J. Org. Chem.* 31, 205 (1966); Horowitz, J. P. et al., *J. Org. Chem.* 32, 817 (1967); and Horowitz, et al., *J. Am. Chem. Soc.* 86, 1896 (1964).

In recent years, some 2',3'-dideoxydidehydro nucleosides have been obtained directly from the corresponding ribonucleosides through their reaction with acetoxyisobutyryl halides, followed by the reductive elimination of the 2'(3')-acetoxy-3'(2')-halogeno derivatives with chromous ion. U.S. Pat. No. 3,817,982 (1974); *Chem. Abstr.* 81, 63942 (1974); Russell, A. F., et al., *J. Am. Chem. Soc.* 95, 4025 (1973); Jain, T. C., et al., *J. Org. Chem.* 39, 30 (1974); Classon, B., et al., *Acta Chem. Scand. Sect B* 32, 251 (1982); Robins, M. J., et al., *Tetrahedron Letters* 25, 367 (1984). In a variation of this method, zinc in dimethylformamide can be used instead of chromous acetate. Robbins, M. et al., *Tet. Letters* 25, 367 (1984). Though this method has been effective for the preparation of 2',3'-didehydrodideoxyadenosine and uridine, its applicability for the synthesis other unsaturated nucleosides such as inosine and guanosine has been very poor. Jain, et al., *J. Org. Chem.* 39, 20 (1974). Further, the reaction is difficult, and results in several products, and is therefore an inefficient route to obtain the 2',3'-unsaturated compounds.

2',3'-Dideoxynucleosides have been obtained through the Barton deoxygenation of dithiocarbonates or thionocarbonates of 2'-deoxynucleosides in 40–55% yield. Prisbe, E. J., and Martin, J. C., *Synth. Commun.* 15, 401 (1985); Webb, R. R., et al., *Nucleosides Nucleotides* 7, 147 (1988). However, the Barton scheme does not provide a route to 2',3'-didehydrodideoxynucleosides.

Therefore, it is an object of the present invention to provide a general synthetic method for both 2',3'-dideoxy and 2',3'-didehydrodideoxy nucleosides from the corresponding ribonucleosides.

It is another object of the present invention to provide a method for the synthesis of 2',3'-dideoxy and 2',3'-dideoxydidehydro nucleosides which is facile and efficient.

It is a further object of the present invention to provide a method of synthesis of 2',3'-dideoxy and 2',3'-dideoxydidehydro nucleosides which is applicable to both purine and pyrimidine nucleosides.

SUMMARY OF THE INVENTION

The present invention provides a general method of synthesis of 2',3'-didehydrodideoxynucleosides, (2',3'-unsaturated nucleosides) which may be reduced to the corresponding 2',3'-dideoxynucleosides (2',3'-saturated nucleosides). The method of synthesis is applicable to both purine and pyrimidine nucleosides.

Briefly, the method for preparing 2',3'-didehydrodideoxynucleosides and the corresponding reduced 2',3'-dideoxynucleosides includes:

i) preparing a nucleoside derivative of the general structure

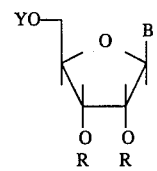

wherein B is a nitrogen, oxygen, or sulfur heterocycle of $C_1$ to $C_{15}$, Y is a suitable oxygen protecting group, each R is C(S)SR' where R' is an alkyl or cyanoalkyl group of $C_1$ to $C_{15}$, or both Rs together are >C=S,; and then ii) deoxygenating the nucleoside derivative to the corresponding 2',3'-didehydrodideoxynucleoside.

The method includes first blocking the 5'-OH group with a silyl or acyl group. Amino groups present in the organic base of the nucleoside can also be protected with a suitable protecting group. The nucleoside is then reacted with carbon disulfide and an alkyl or substituted alkyl halide in base to produce the corresponding dialkyl xanthate nucleoside. On treatment with azabisisobutyronitrile and tributyltin hydride, the dialkyl xanthate nucleoside is deoxygenated to the corresponding 2',3'-didehydrodideoxy nucleoside. Removal of the protecting groups followed by reduction of the 2',3'-didehydrodideoxynucleoside produces a 2',3'-dideoxynucleoside.

A second embodiment of the present invention includes the preparation of a 2',3'-cyclic thiocarbonate nucleoside by reaction of the 5'-silyl protected nucleoside with thiocarbonyldiimidazole, or by isolation as a minor product in the above described dialkyl xanthate reaction. The 2',3'-cyclic thiocarbonate nucleoside is deoxygenated under mild conditions with triethyl phosphite or 1,3-dimethyl-2-phenyl-1,3,2,-diazaphospholidine to form the 2',3'-didehydrodideoxy nucleoside, which may then be reduced to the 2',3'-dideoxy nucleoside after removal of the protecting groups.

DETAILED DESCRIPTION OF THE INVENTION

Figure 1:
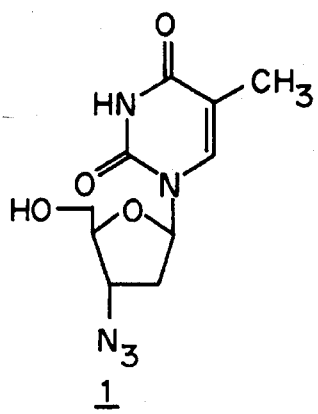
FIG. 1 is an illustration of selected 2',3'-dideoxy- and 2',3'-dideoxydidehydro- nucleosides which may be prepared according to the method of synthesis of the present invention.
Figure 1:
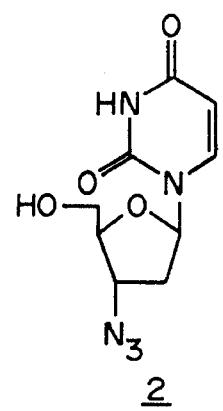
Figure 1:
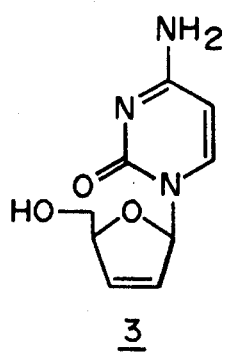
Figure 1:
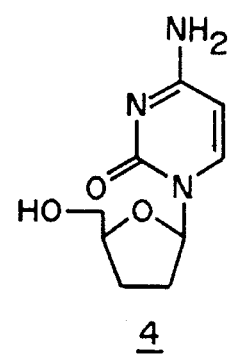
Figure 1:
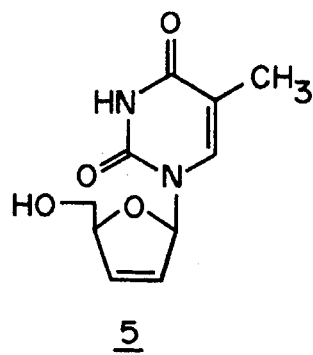
Figure 1:
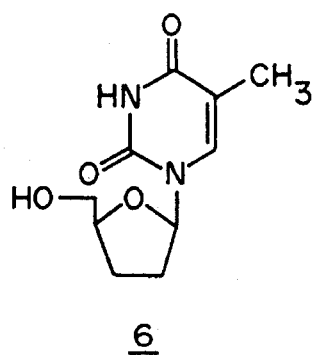
Figure 1:
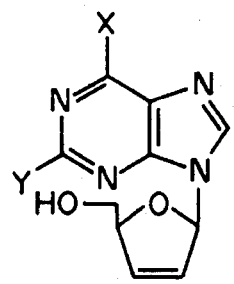
Figure 1:
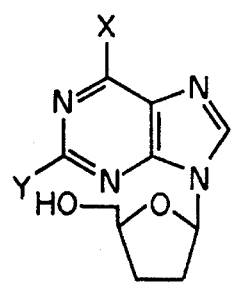

The present invention is a general method of synthesis of 2',3'-didehydrodideoxynucleosides, which can be reduced to the corresponding 2',3'-dideoxynucleosides. The method of synthesis is applicable to both purine and pyrimidine nucleosides, such as inosine, guanosine, cytidine, uridine, thymidine and adenosine, and is more efficient than the methods presently used to produce such compounds.

Barrett, et al., *J. Chem. Soc. Chem. Commun.* 866 (1977); Barrett, et al., *J. Chem. Soc. Chem. Perkin Trans. I* 2378 (1979) and Hayashi, et al., *Chem. Pharm. Bull. Japan* 26, 1786 (1978) reported the synthesis of olefinic carbohydrates and aminoglycosides from the corresponding vicinal-diols through dialkyl xanthate intermediates. However, this method has never been extended to the preparation of unsaturated nucleosides. It has now been discovered that a wide variety of 2',3'-didehydrodideoxy nucleosides may be prepared from their corresponding nucleosides through dialkyl xanthate intermediates in good yields.

The method for preparing 2',3'-didehydrodideoxynucleosides and the corresponding reduced 2',3'-dideoxynucleosides includes:

i) preparing a nucleoside derivative of the general structure

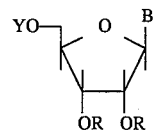

wherein B is a nitrogen, oxygen, or sulfur heterocycle of $C_1$ to $C_{15}$, Y is a suitable oxygen protecting group, each R is $C(S)SR'$ wherein R' is an alkyl or cyanoalkyl group of $C_1$ to $C_{15}$ or both Rs together are $>C=S$, ; and then ii) deoxygenating the nucleoside derivative to the corresponding 2',3'-didehydrodideoxynucleoside.

For example, B can be a nitrogenous heterocycle such as a purine, pyrimidine, pyridine, pyrrole, indole, imidazole, pyrazole, quinazoline, pyridazine, pyrazine, cinnoline, phthalazine, quinoxaline, xanthine, hypoxanthine, adenine, guanine, cytosine, uracil, thymine, pteridine, 5-azacytidine, 5-azauracil, triazolopyridine, imidazolopyridine, imidazolotriazine, pyrrolopyrimidine, or pyrazolopyrimidine.

Alternatively, B can be an oxygen heterocycle such as furan or benzofuran, a mixed oxygen-nitrogen heterocycle such as oxazole or isoxazole, or an oxygen-sulfur heterocycle. In addition, B can be a sulfur heterocycle such as thiophene or benzothiophene, or a sulfur-nitrogen heterocycle such as thiazole or isothiazole.

These heterocycles can be substituted with alkyl groups or aromatic rings, bonded through single or double bonds or fused to the heterocyclic ring system. The heterocycle may be bound to the β-D-ribofuranoside in the nucleoside through any available atom, including ring nitrogen and ring carbon (producing a C-nucleoside).

The method of synthesis includes, first, protecting the 5' position of the nucleoside with a suitable oxygen protecting group, preferably with an acyl or silyl group, by methods well known to those skilled in the art. For example, chloro-t-butyl dimethylsilane may be reacted with the nucleoside to form the corresponding 5'-t-butyl dimethyl silyl nucleoside.

The amino group of the organic base in the nucleoside, if any, may then be blocked by reaction with benzoyl chloride or any other suitable acyl compound. Generally, it is necessary to block the amino groups on pyrimidines but not purines, because amino groups on pyrimidines are more reactive.

The resulting N-blocked-5'-blocked nucleoside is then reacted with carbon disulfide in base, followed by treatment with an alkyl or substituted alkyl halide, to form a 2',3'-dialkyl xanthate nucleoside. Examples of suitable alkyl halides that may be used in this step are methyl iodide and 3-haloproprionitrile. The latter is especially useful for uridines and ribosyl thymine, because it prevents alkylation at the $N_3$ position.

If alkylation at the $N^6$ position of adenosine is desired, 5'-protected adenosine can be reacted with benzoyl chloride to produce $N^6$-dibenzoyl-5'-protected adenosine. This compound is then reacted with carbon disulfide and alkyl halide to form the $N^6$-methyl,benzoyl- 5'-protected-2',3'-dialkyl xanthate derivative, which is deoxygenated and deprotected to produce $N^6$-methyl-2',3'-didehydrodideoxy adenosine.

The 2',3'-dialkyl xanthate nucleoside produced as described above is treated with azabisisobutyronitrile and tributyltin hydride to produce the corresponding 2',3'-unsaturated nucleoside. The protecting acyl or silyl groups on the 5' position and on the amino group of the organic base may then be removed by methods known to those skilled in the art.

If the 2',3'-dideoxy nucleoside is desired, the 2',3'-unsaturated nucleoside prepared according to this method may be reduced. For example, hydrogen reduction may be effected in ethanol with 10% palladium on carbon.

A second embodiment of the present invention includes the preparation of a 2',3'-cyclic thiocarbonate nucleoside by reaction of the 5'-silyl protected nucleoside with thiocarbonyldiimidazole, or by isolation as a minor product in the above described nucleoside reaction which produces the dialkyl xanthate nucleoside. The 2',3'-cyclic thiocarbonate nucleoside is deoxygenated under mild conditions with triethyl phosphite or 1,3-dimethyl-2-phenyl- 1,3,2,-diazaphospholidine to form the 2',3'-unsaturated nucleoside, which may then be reduced to the 2',3'-saturated nucleoside after removal of the protecting groups.

The 2',3'-cyclic thiocarbonate of uridine has been prepared, Ruyle, et al., *J. Org. Chem.* 35, 3558 (1970), but the yield was low when Raney nickel was used for the deoxygenation and N$_3$-methylation was observed when trimethyl phosphite was employed instead of Raney nickel. Similar deoxygenation of 2',3'-thionocarbonate of adenosine employing Raney nickel failed to yield 2',3'-didehydro-2', 3'-dideoxyadenosine. Tong, et al., *J. Orq. Chem.* 30, 2854 (1965).

It has now been discovered that when triethyl phosphite is used in place of trimethyl phosphite to deoxygenate the 2',3'-cyclic thiocarbonate, nitrogen alkylation on the organic base does not occur.

Examples of compounds, illustrated in FIG. 1, which may be prepared according to the present invention include 3'-azido-3-deoxythymidine (1), 3'-azido- 2',3'-dideoxyuridine (2), 2',3'-dideoxycytidine (3), 2',3'-dideoxycytidine (4), 2',3'-didehydrodideoxythymidine (5), 2',3'-dideoxythymidine (6), 2',3'-didehydrodideoxyadenosine (7), 2',3'-didehydrodideoxyinosine (8), 2',3'-didehydrodideoxy (9), 2',3'-dideoxyadenosine (10), 2',3'-dideoxyinosine (11), and 2',3'-dideoxyquanosine (12).

The following working examples provide a further understanding of the method of the present invention. These examples are illustrative only, and are not meant to limit the scope of the invention. Equivalent or similar solvents and reagents may be substituted for those particular solvents and reagents described herein without departing from the intended general scope of the method of synthesis.

Melting points were determined on a Thomas Hoover capillary apparatus and are uncorrected. $^1$H NMR spectra were recorded on a Jeol FX 90Q Fourier transform spectrometer or a Bruker AM 250 NMR spectrometer for the 90- and 250 MHz $^1$H NMR, respectively, using tetramethylsilane as an internal standard; chemical shifts are reported in parts per million (δ) and signals are quoted as s (singlet), d (doublet), t (triplet), q (quartet) or m (multiplet). UV spectra were taken on a Bausch and Lomb Spectronic 2000 spectrometer. IR spectra were measured on a Perkin-Elmer 684 spectrophotometer. Optical rotations were measured on a Perkin-Elmer 141 polarimeter. TLC (thin layer chromatography) was performed on Uniplates purchased from Analtech Co. Elemental analyses were performed by Atlantic Microlab Inc., Atlanta, Ga. The abbreviation "THF" refers to tetrahydrofuran, and "DMSO" refers to dimethylsulfoxide.

Preparation of 2',3'-Didehydrodideoxyadenosine

Figure 2:
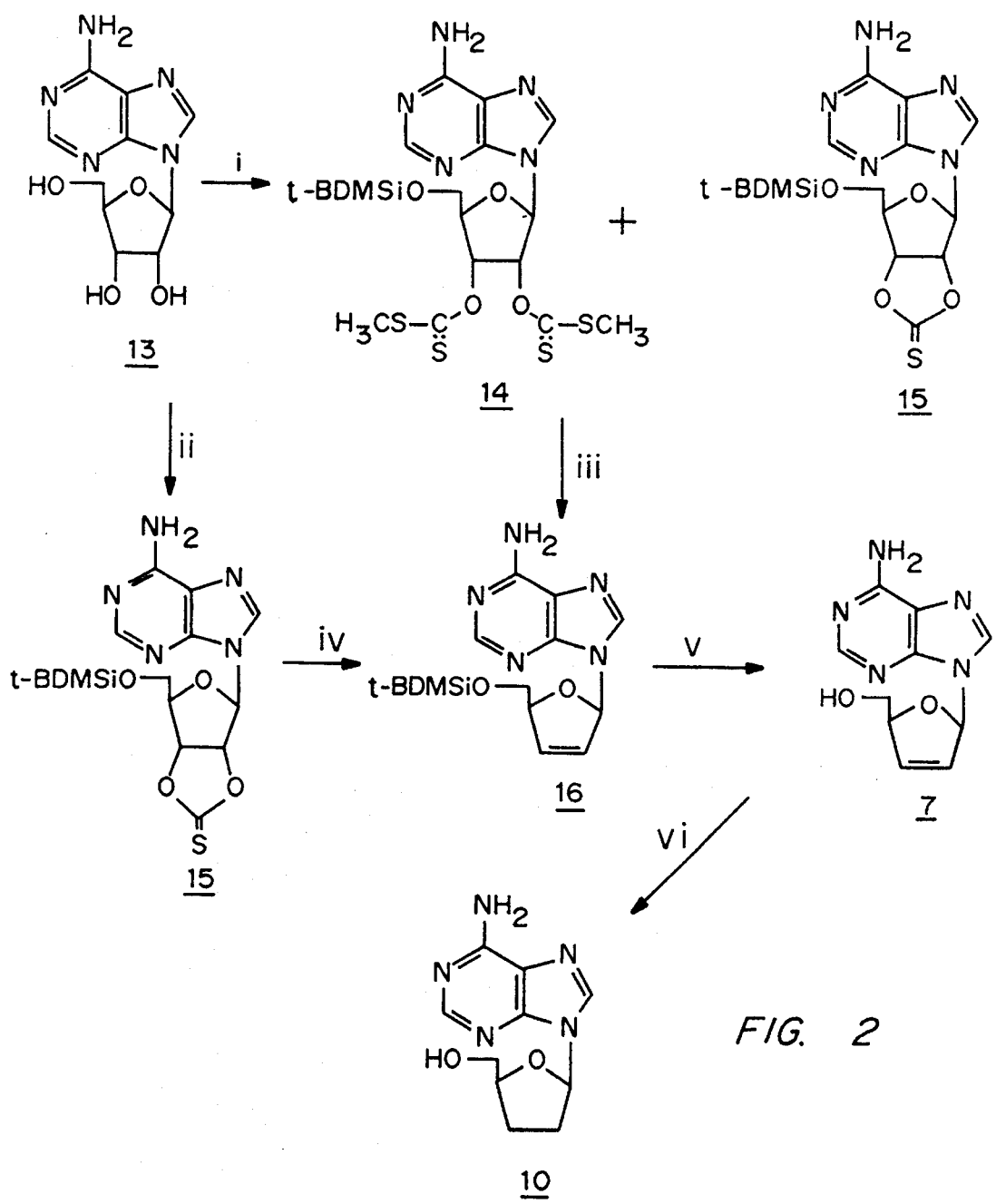
FIG. 2 is an illustration of Scheme 1 according to the present invention for the synthesis of 2',3'-dideoxyadenosine

In Scheme 1, as illustrated in FIG. 2, 5'-O-tbutyldimethylsilyl adenosine was reacted with carbon disulfide in the presence of 5 N sodium hydroxide and then alkylated in situ with methyl iodide to give the dimethyl xanthate derivative 14 in moderate yield (70%) A minor product, 2',3'-O-thionocarbonate 15 was also obtained (11.7%) in this reaction. Subsequently, 15 was prepared by the reaction of 5'-O-t-butyldimethylsilyl adenosine with thiocarbonyldiimidazole in 73.5% yield.

The dimethyl xanthate 14 on treatment with tri-n-butyl tin hydride in refluxing toluene gave a good yield (93%) of 5'-O-tert-butyldimethylsilyl-2',3'-didehydro- 2',3'-dideoxyadenosine 16 after silica gel column chromatography. Thionocarbonate 15 was also deoxygenated to 16 under mild conditions using 1,3-dimethyl- 2-phenyl-1,3,2-diazaphospholidine. However, this reaction gave a lower yield (51%) of 16 than the dialkyl xanthate method.

Attempted reduction of 16 to the corresponding saturated adenosine analogue was not successful possibly due to the presence of a small amount of residual sulfur by-product or due to the steric hindrance caused by the bulky 5'-silyl groups as well as the adenine moiety. It is well known that catalytic hydrogenation is sensitive to the steric hindrance. Therefore, the unsaturated nucleoside 16 was desilylated to 7 and then reduced to 2',3'-dideoxyadenosine (10).

The following is a working example for the preparation of 2',3'-didehydro- and 2',3'-didehydrodideoxyadenosine.

5'-O-tert-Butyldimethylsilyl-2,,3,-bis-O[ (methylthio-)thiocarbonyl]adenosine (14) and 5'-O-tert-Butyldimethylsilyl- 2',3,-Othionocarbonyladenosine (15).

To a stirred suspension of adenosine (13) (10.0 g, 37.4 mmol) and imidazole (6.12 g, 90 mmol) in DMF (200 ml) was added tert-butyldimethylsilyl chloride (6.78 g, 45 mmol). The reaction mixture was stirred under anhydrous conditions for 20 h. The solvent was removed under vacuum and the residue was purified by flash vacuum chromatography over silica using $CHCl_3$-methanol (30:1) as the eluent. Evaporation of the appropriate fractions and the trituration of the residue with hexanes yielded 11.66 g (81.83%) of 5'-O-tertbutyldimethylsilyladenosine as a colorless solid.

To a solution of 5'-O-tertbutyldimethylsilyladenosine (3.0 g, 7.87 mmol) and $CS_2$ (2.0 g, 26.4 mmol) in DMSO (20 ml), maintained at 15° C, was added dropwise aqueous 5N NaOH solution (3.5 ml). The mixture was stirred for 20 min and treated dropwise with $CH_3I$ (2.46 g, 17.03 mmol). The stirring was continued for 1 h, the solvent was removed in vacuo, and the residue was extracted with ethyl acetate. The organic layer was washed with water, dried ($MgSO_4$), and concentrated. Purification of the oily residue by flash vacuum chromatography on a silica gel column using $CHCl_3$-methanol (20:1) as the eluent gave 3.09 g (70%) of 14 and 0.39 g (11.7%) of 15. 2',3'-Bis-O-dithiocarbonate 14 mp 164°–165° C. (benzene-hexane); $^1$H NMR ($CDCl_3$) δ 0.04 (6H, s, $(CH_3)_2Si$), 0.97 (9H, s, $(CH_3)_3CSi$), 2.53 (3H, s, $SCH_3$), 2.61 (3H, s, $SCH_3$), 4.01 (2H, m, 5'-H), 4.53 (1H, m, 4'-H), 5.90 (2H, br s, $NH_2$), 6.45–6.66 (2H, m, 1',2', and 3'-H), 8.21 (1H, s, 8-H), 8.38 (1H, s, 2-H).

Analysis Calculated for $C_{20}H_{31}N_5O_4S_4Si$: C, 42.78; H, 5.53; N, 12.48; S, 22.82. Found: C, 42.77; H, 5.56; N, 12.43; S, 22.74.

Thionocarbonate 15: mp 198°–199° C. ($CHCl_3$); UV (ethanol) λmax (pH 1) 238 nm, 254 (sh); (pH 7) 239, 255 (sh); (pH 12) 229, 258; $^1$H NMR ($CDCl_3$) δ 0.0 (6H, s, $(CH_3)_2Si$), 0.83 (9 h, S, $(CH_3)_3CSi$), 3.70 (2H, d,J =6 Hz, 5'-H), 4.59 (1H, dt, J=2.5 Hz, 6 Hz, 4'-H), 5.77 (2H, br s, $NH_2$), 5.80 (1H, dd, J=2.5 Hz, 7 Hz, 3'-H), 6.30 (1H, d, J=1.5 Hz, 1'-H), 6.39 (1 H, dd, J=1.5 Hz, 7 Hz, 2'-H), 7.92 (1H, s, 8-H), 8.32 (1H, s, 2-H).

Analysis Calculated for $C_{17}H_{25}N_5O_4SSi$: C, 48.20; H, 5.95; N, 16.54; S, 7.57. Found: C, 48.25; H, 5.97; N, 16.51; S, 7.63.

5'-O-tert-Butyldimethylsilyl-2',3'-O-thionocarbonyl-adenosine (15)

To a solution of 5'-O-tert-butyldimethylsilyladenosine (0.38 g, 1.0 mmol) in DMF (5 ml) was added thiocarbonyldiimidazole (0.2 g, 1.12 mmol) and the mixture was heated at 80° C. for 1 h. The solvent was removed under vacuum and the residue was triturated with $CHCl_3$ (3 ml). The solid obtained was filtered, dried, and recrystallized from $CHCl_3$ to give 0.31 g (73.5%) of 15 as white needles: mp 199°–200° C.

5'-O-tert-Butyldimethylsilyl-2',3'-didehydro-2',3'-dideoxyadenosine (16)

Method A: From 2',3'-O-bisdithiocarbonate 14. A solution of tri-n-butyltin hydride (15.0 g, 51.56 mmol) and azobisisobutyronitrile (0.8 g) in dry toluene (100 ml) was added dropwise over one hour to a solution of 14 (7.23 g, 12.89 mmol) in dry toluene (100 ml) at reflux. The solvent was removed under vacuum and the residue was chromatographed on a silica gel column using 0–3% methanol in $CHCl_3$. Evaporation of the appropriate fractions and recrystallization of the residue from benzene yielded 4.18 g (93%) of 16 as a crystalline product: mp 117°–121° C.; $^1H$ NMR (DMSO-$d_6$) δ 0.02 (6H, s, $(CH_3)_2Si$), 0.85 (9H, s $(CH_3)_3CSi$), 3.80, (2H, d, J=3.96 Hz, 5'-H), 4.80–5.00 (1H, m, 4'-H), 6.24 (1H, dt, J=1.6 Hz, 6.15 Hz, 2'-H), 6.44 (1H, dt, J=1.6 Hz, 6.15 Hz, 3'-H), 6.97 (1H, m, 1'-H), 7.27 (2H, br s, $NH_2$), 8.12 (1H, s, 8-H), 8.19 (1H, s, 2-H).

Analysis Calculated for $C_{16}H_{25}N_5O_2Si$: C, 55.31; H, 7.25; N, 20.15. Found: C, 55.21; H, 7.27; N, 20.07.

Method B: From 2',3'-O-thionocarbonate 15. To a solution of 15 (0.65 g, 1.5 mmol) in dry THF (5 ml), cooled to 0° C., was added dropwise 1,3-dimethyl-2-phenyl- 1,3,2-diazaphospholidine (0.9 g, 4.6 mmol). The reaction mixture was stirred under nitrogen at 0° C. for 10 minutes and then at room temperature for 3 h. The solvent was removed under vacuum and the oily residue was purified by chromatography on a silica gel column using 4% methanol in ethyl acetate as the eluent. Evaporation of the appropriate fractions and crystallization of the residue from benzene yielded 0.27 g (51%) of 16.

The use of triethyl phosphite at 150° C. instead of 1,3-dimethyl-2-phenyl-1,3,2-diazaphospholidine afforded a 34% yield of 16.

2',3'-Didehydro-2',3'-dideoxyadenosine (7)

To a solution of 16 (3.79 g, 10.92 mmol) in dry THF (40 mL), cooled in an ice-bath, was added 22 ml of a 1M solution of tetra-n-butylammonium flouride in THF (22 mL, 22.0 mmol). The mixture was stirred for 40 minutes at room temperature and concentrated. The resulting yellow syrupy residue was purified by chromatography on a silica gel column using a gradient of 3–5% methanol in $CHCl_3$. Evaporation of the appropriate fractions yielded 2.21 g (86%) of 7: mp 184°–186° C. (methanol); $^1H$ NMR (DMSO-$d_6$) δ 3.59 (2H, dd, J=4.1 Hz, 5.27 Hz, 5'-H), 4.80–5.10 (2H, m, 4'-H and OH), 6.14 (1H, ddd, J=1.46 Hz, 1.76 Hz, 5.86 Hz, 2'-H), 6.47 (1H, ddd, J=1.46 Hz, 1.76 Hz, 5.87 Hz, 3'-H), 6.94 (1H, m, 1'-H), 7.25 (2H, br s, $NH_2$), 8.157 (1H, s, 8-H), 8.167 (1H, s, 2-H).

2',3'-Dideoxyadenosine (10)

A solution of 7 (1.27 g) in methanol (325 ml) was hydrogenated at 15 psi in the presence of 10% Pd/C (0.65 g). The reaction mixture was filtered through celite and the filtrate was evaporated. Crystallization of the crude product from methanol gave 0.57 g of 10: mp 186°–188° C. (Lit. mp 185°–187° C.)

Preparation of 2',3'-Dideoxydidehydroinosine

Figure 3:
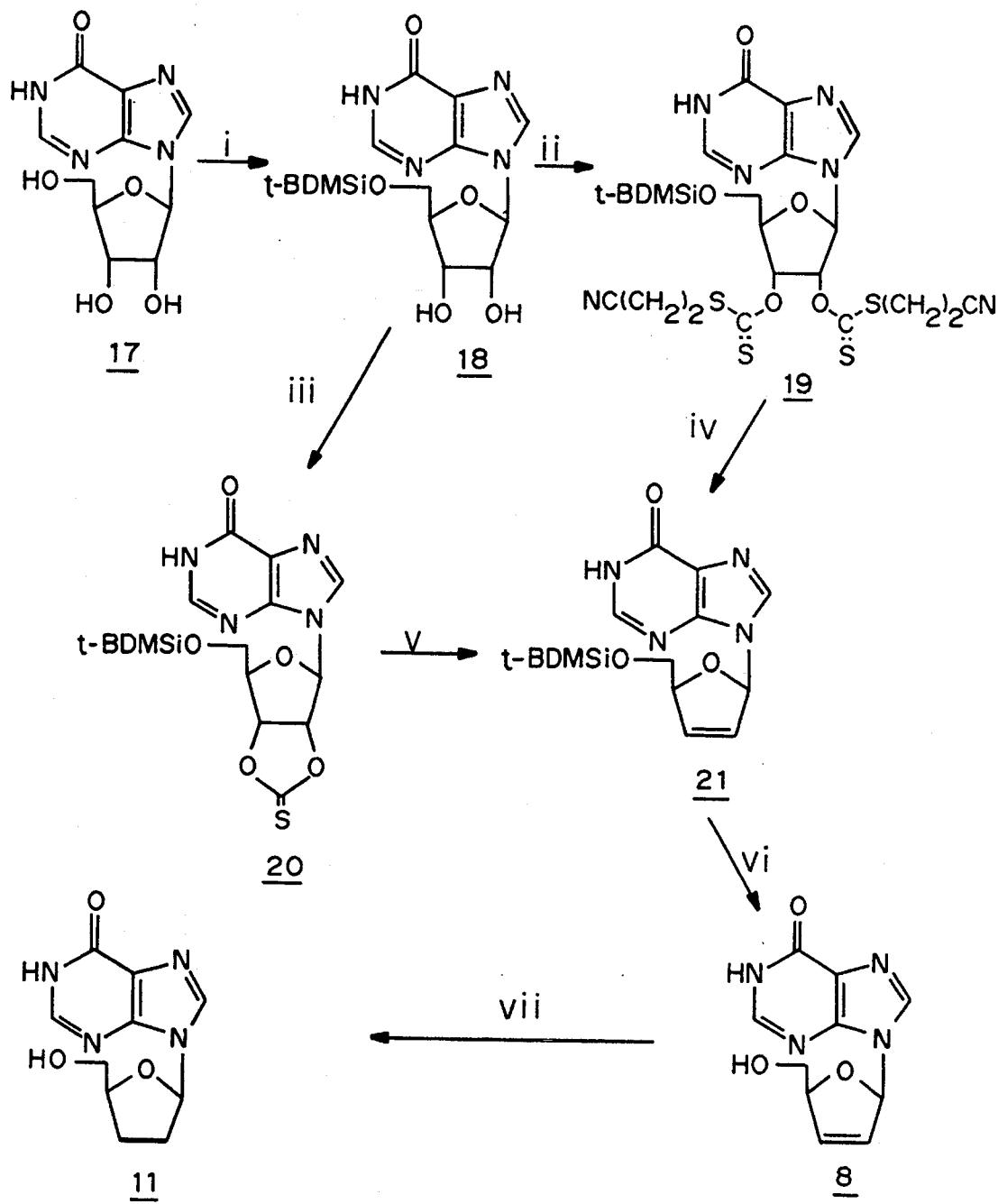
FIG. 3 is an illustration of Scheme 2 according to the present invention for the synthesis of 2',3'-dideoxyinosine

FIG. 3 is an illustration of Scheme 2 according to the present invention for the synthesis of 2',3'-dideoxyinosine In the case of inosine, the dialkyl xanthate (19) was prepared using β-bromopropionitrile instead of methyl iodide in order to avoid N-methylation as observed in uridine when methyl iodide was employed as the alkylating agent (Scheme 5). The 5'-O-t-butyldimethylsilyl inosine 18 was treated with carbon disulfide in the presence of sodium hydroxide and alkylated in situ with bromopropionitrile to obtain 19 in 61% yield after silica gel chromatography. No nitrogen alkylated product was observed. Even if the alkylation at nitrogen did occur, the cyanoethyl group would be eliminated under the basic conditions used. The dialkyl xanthate 19 was found to undergo facile deoxygenation with tributyltin hydride to give 2',3'-unsaturated nucleoside 21 in 85% yield. The unsaturated inosine derivative 21 was also obtained, although in lower yield (39%), from the thionocarbonate 20 by deoxygenation with triethyl phosphite 5'-Desilylation of 21 to 2',3'-didehydro- 2',3'-dideoxyinosine (8) followed by catalytic reduction gave the 2',3'-dideoxyinosine (11) in 78% yield.

In handling 2',3'-unsaturated nucleosides, care should be taken to avoid deglycosylation in protic solvents. This is especially true for the inosine derivative 8, which is unusually unstable in a protic environment.

The following working example further describes the synthesis of 2',3'-didehydrodideoxy inosine according to the present invention.

5'-O-tert-Butyldimethylsilylinosine (18)

A mixture of inosine 13 (15.0 g, 56 mmol) (dried by coevaporation with 70 ml of dimethylformamide (DMF)), imidazole (9.52 g, 140 mmol) and tertbutyldimethylsilyl chloride (10.1 g, 67 mmol) in DMF (125 ml) was stirred at room temperature for 12 h. The solvent was removed in vacuo and the residue was purified chromatographically using $CHCl_3$-methanol (15:2) as the eluent to obtain 16.4 g (76.7%) of 18: mp softening at 220° C., melting at 229°–231° C. ($CHCl_3$-diethyl ether); $^1H$ NMR (DMSO-$d_6$) δ 0.0 (6H, s, $(CH_3)_2Si$), 0.82 (9H, s, $(CH_3)_3CSi$), 3.52–4.00 (3H, m, 4' and 5'-H), 4.10 (1H, t, J=4.8 Hz, 2'(3')-H), 4.41 (1H, t, J=4.8 HZ, 3'(2')-H), 5.83 (1H, d, J= 5.3 HZ, 1'-H), 8.00 (1H, s, 8-H), 8.18 (1H, s, 2-H).

Analysis Calculated for $C_{16}H_{26}N_4O_5Si$: C, 50.24; H, 6.85; N, 14.65. Found: C, 50.16; H, 6.85:N, 14.63.

5'O-tert-Butyldimethylsilyl-2',3'-bis-O-[β-cyanoethylthio)thiocarbonyl] inosine (19)

To an ice-cooled solution of 18 (10.0 g, 26 mmol) and $CS_2$ (28 ml) in dimethyl sulfoxide (DMSO) (75 mL) under nitrogen was added 5N aqueous NaOH solution (28 mL). After stirring for 35 min, β-bromopropionitrile (73 mL) was added to the reaction mixture and the stirring was continued for an additional 40 min. The reaction mixture was diluted with ice-cold water and extracted with ethyl acetate. The organic layer was washed with water, dried over $MgSO_4$, and concentrated. Column chromatography over silica using $CHCl_3$-methanol (20:1) as the eluent yielded 10.2 g (61%) of 19: mp 150°–155° C. dec ($CHCl_3$-diethyl ether); $^1H$ NMR (DMSO-$d_6$) δ 0.0 (6 H, s, $(CH_3)_2Si$), 0.79 (9H, s, (CH$_3$)$_3$CSi), 2.69–3.60 (8H, m, CH$_2$CH$_2$CN), 3.91 (2H, d, J=2.4 Hz, 5'-H), 4.56 (1H, m, 1'-H), 6.23–6.71 (3H, m, 1',2', and 3'-H), 7.98 (1H, s, 8-H), 8.16 (1H, s, 2-H).

Analysis Calculated for C$_{24}$H$_{32}$N$_6$O$_5$S$_4$Si: C, 44.98; H, 5.03; N, 13.11. Found: C, 45.05; H, 5.05; N, 13.08.

5'-O-tert-Butyldimethylsilyl-2',3'-O-thionocarbonyl-inosine (20)

A solution of 18 (4.6 g, 12.04 mmol) and thiocarbonyl-diimidazole (4.2 g, 23.6 mmol) in DMF (50 ml) was stirred at room temperature for 12 h. The solvent was removed under vacuum and the residue was taken up in CHCl$_3$. The organic layer was washed with water and dried (Na$_2$SO$_4$). Evaporation of CHCl$_3$ and the purification of the residue by flash chromatography over silica using CHCl$_3$-methanol (17:1) as the eluent afforded 2.76 g (54%) of 20: mp 173°–175° C. (CHCl$_3$-diethyl ether); UV (methanol) λmax (pH 3) 272 nm (sh), 240; (pH 7) 272 (sh), 240; (pH 11) 252, 235 (sh); $^1$H NMR (DMSO-d$_6$) δ 0.05 (6H, s, (CH$_3$)$_2$Si), 0.84 (9H, s, (CH$_3$)$_3$CSi), 3.83 (2H, d, J =5.57 Hz, 5'-H), 4.55–4.75 (1H, m, 4'-H), 5.79 (1H, dd, J=2.35 Hz, 7.32 Hz, 3'-H) 6.28 (1H, dd, J= 1.76 Hz, 7.32 Hz, 2'-H), 6.59 (1H, d, J=1.76 Hz, 1'-H), 8.15 (1H, s, 8-H), 8.26 (1H, s, 2-H), 12.50 (1H, br s, NH, exchangeable).

Analysis Calculated for C$_{17}$H$_2$N$_4$O$_5$SSi: C, 48.10; H, 5.70; N, 13.20; S, 7.55. Found: C, 47.98; H, 5.75; N, 13.14; S, 7.48.

5'-O-tert-Butyldimethylsilyl-2',3'-didehydro-2',3'-dideoxyinosine (21)

Method A: From 2',3'-O-dithiocarbonate 19. To a solution of 19 (5.0 g, 7.8 mmol) in dry toluene (140 ml), at 100° C., under nitrogen was added dropwise a solution of tri-n-butyltin hydride (17.3 g, 59 mmol) and azobisisobutyronitrile (1.5 g) in dry toluene (10 ml). The reaction mixture was refluxed for 1.5 h and cooled. The solvent was removed under vacuum and the residue was purified by flash chromatography on a silica gel column using CHCl$_3$-methanol (20:1) to yield 2.3 g (85%) of the olefin 21: mp 178°–180° C. (methanol-acetone); $^1$H NMR (CDCl$_3$) 0.03 (6H, s, (CH$_3$)$_2$Si), 0.85 (9H, s, (CH$_3$)$_3$CSi), 3.79, (2H, d, J =3.8 Hz, 5'-H), 4.96 (1H, m, 4'-H), 6.22 (1H, dt, J =1.5 Hz, 5.86 Hz, 2'-H), 6.52 (1H, dt, J=1.5 Hz, 5.86 Hz, 3'-H), 6.95 (1H, m, 1'-H), 8.06 (1H, s, 8-H), 8.11 (1H, s, 2-H), 12.30 (1H, br s, NH, exchangeable).

Analysis Calculated for C$_{16}$H$_{24}$N$_4$O$_3$Si: C, 55.15; H, 6.94; N, 16.08. Found: C, 55.02; H, 6.99; N, 16.03.

Method B: From 2',3'-O-thionocarbonate 20. A solution of 2.0. (1.0 g, 2.4 mmol) in triethyl phosphite (30 ml) was heated to gentle reflux under nitrogen for 30 min. Excess reagent was evaporated under reduced pressure and the residue was purified by flash chromatography on a silica gel column using CHCl$_3$-methanol (15:1) to obtain 0.32 g (39%) of 21.

2',3'-Didehydro-2',3'-dideoxyinosine (8)

To a solution of 21 (3.0 g, 8.6 mmol) in dry tetrahydrofuran (THF) (65 ml), cooled in an ice-bath, was added a 1M solution of tetra-n-butylammonium fluoride in THF (34 ml, 34.0 mmol). The mixture was stirred at 0° C. for 30 minutes, and the solvent was evaporated under vacuum. The residue was purified by chromatography on a silica gel column using CHCl$_3$methanol (7:1) as the eluent. Concentration of the TLC purified fractions yielded 1.36 g (67%) of 8: mp >310° C. (methanol); $^1$H NMR (DMSO-d$_6$) δ 3.56 (2H, d, J =2.6 Hz, 5'-H), 4.84 (2H, m, 4'-H and OH, collapses to a multiplet integrating to one proton after D$_2$O exchange), 6.12 (1H, br d, J=5.7 Hz, 2'-H), 6.47 (1 H, br d, J=5.7 Hz, 3'-H), 6.90 (1H, m, 1'-H), 8.06 (1H, s, 8-H), 8.10 (1H, s, 2-H), 12.40 (1H, br s, NH).

Analysis Calculated for C$_{10}$H$_{10}$N$_4$O$_3$: C, 51.28; H, 4.30; N, 23.92. Found: C, 51.30; H, 4.32; N, 23.84.

2',3'-Dideoxyinosine (11)

A solution of the olefin 8 (0.38 g, 1.6 mmol) in a mixture of ethanol-water (4:1) (70 ml) was hydrogenated in the presence of 10% Pd/C (0.07 g) at 50 psi for 6 h. The mixture was filtered through celite, the filtrate was concentrated, and cooled. The solid obtained was filtered and dried to yield 0.3 g (78%) of 11: mp softens at 184°–186° C., but does not melt up to 300° C.; $^1$H NMR (DMSO-d$_6$) δ 1.72– 2.48 (4H, m, 2' and 3'-H), 3.21–3.67 (2H, m, 5'-H), 4.17–4.38 (1H, m, 4'-H), 4.72 (1 H br s, OH, exchangeable), 6.20 (1H, dd, J=3.81 Hz, 4.1 Hz, 1'-H), 7.90 (1H, s, 8-H), 8.15 (1H, s, 2-H), 12.20 (1 H, br s, NH).

Analysis Calculated for C$_{10}$H$_{12}$N$_4$O$_3$: C, 50.84; H, 5.12; N, 23.72. Found: C, 50.74; H, 5.15; N, 23.66.

Preparation of 2',3'-Dideoxydidehydroguanosine

Figure 4:
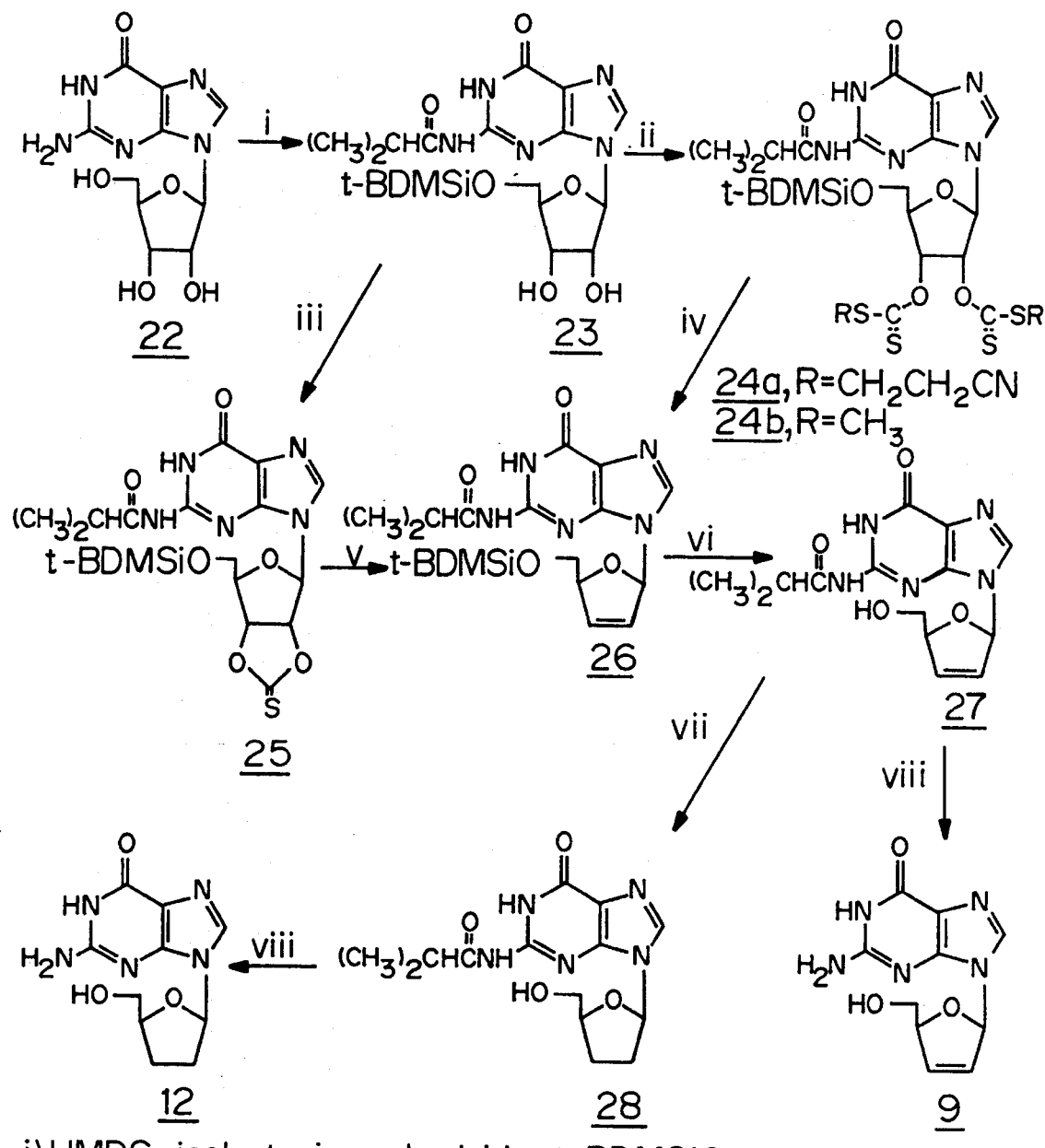
FIG. 4 is an illustration of Scheme 3 according to the present invention for the synthesis of 2',3'-dideoxyguanosine.
Figure 5:
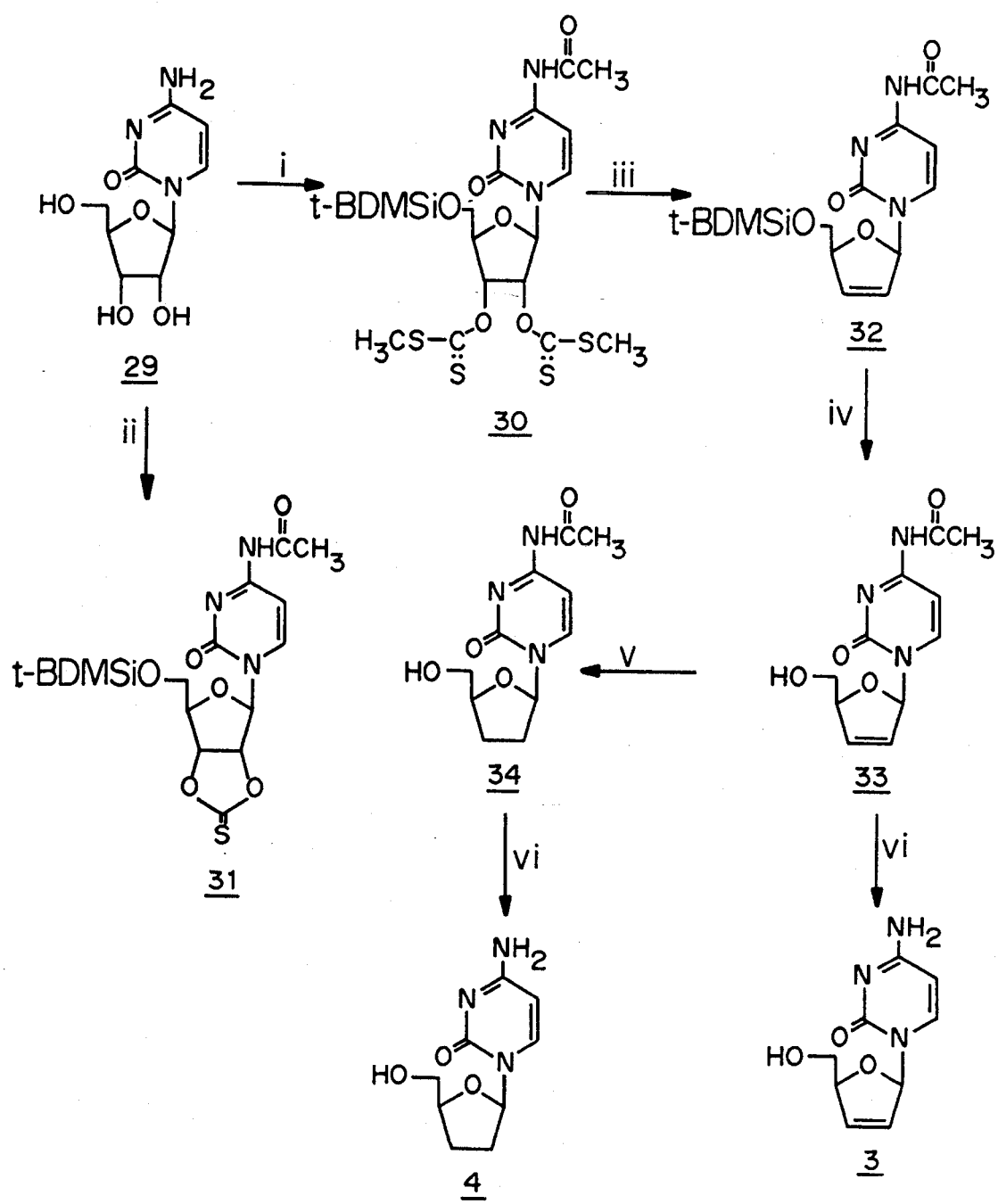
FIG. 5 is an illustration of Scheme 4 according to the present invention for the synthesis of 2',3'-dideoxycytidine

The above method of deoxygenation was extended to guanosine (22) (Scheme 3, FIG. 4). Both β-bromopropionitrile and methyl iodide were found to be suitable reagents for dialkyl xanthate production. Treatment with methyl iodide did not produce the N$^1$-alkylated product, probably due to the adjacent N$^2$-isobutyryl group. Both bisxanthates 24a and 24b gave the unsaturated guanosine derivative 26 in about 50– 55% yield. Conversion of 25 to 26 in refluxing triethyl phosphite was not successful because of the decomposition of 26 under the reaction conditions. However, the use of 1,3-dimethyl-2-phenyl-1,3,2-diazaphospholidine, at room temperature, as the deoxygenating agent afforded 26 in 48% yield.

The following working example further illustrates the synthesis of 2',3'-didehydrodideoxy guanosine according to the present invention.

5'-O-tert-Butyldimethylsilyl-N$^2$-isobutyrylguanosine (23)

To a suspension of guanosine (20.0 g, 70.67 mmol) in dry DMF (75 ml) was added hexamethyldisilazane (110 ml). The mixture was stirred for 30 minutes during which time all of the guanosine went into solution. The mixture was stirred for 12 h, cooled to 10°–15° C., and then treated with dry pyridine (100 mL), followed by isobutyric anhydride (180 ml). The reaction mixture was stirred for 24 h, cooled to 0°–5° C., and treated dropwise with methanol (200 ml). After stirring for 4 h, the mixture was concentrated to about 100 ml, diluted with a mixture of hexanes and diethyl ether (1:1) (500 ml) and left overnight. The gummy product which separated was filtered, triturated with diethyl ether and dried to yield 24 g (96%) of N$^2$-isobutyrylguanosine as a pale yellow solid.

A mixture of N$^2$-isobutyrylguanosine (15.0 g, 42.5 mmol) (dried by coevaporation with 40 ml of DMF), imidazole (7.2 g, 105.9 mmol) and tertbutyldimethylsilyl chloride (6.4 g, 42.5 mmol) in DMF (50 ml) was stirred at room temperature for 12 h. The solvent was removed in vacuo and the residue was dissolved in CHCl$_3$ (300 ml). The organic layer was washed with water, dried (Na$_2$SO$_4$), and concentrated to a syrup. Chromatography on a silica gel column using a gradient of 2.5–7.5% methanol in CHCl$_3$ as the eluent yielded 14.0 g (70.5%) of 23 as a colorless foamy (?) solid; mp 208°–210° C.; $^1$H NMR (DMSO-d$_6$) δ 0.05 (6H, s, (CH$_3$)$_2$Si), 0.88 (9H, s, (CH$_3$)$_3$CSi), 1.12 (6H, d, J =6.74 Hz, (CH$_3$)$_2$C), 2.78 (1H, septet, J=6.74 Hz, (CH$_3$)$_2$CH), 3.60–4.00 (3H, m, 4' and 5'-H), 4.15 (1H, m, 3'-H), 4.40 (1H, m, 2'-H), 5.30 (1H, br m, OH), 5.85 (1H, d, J=5.28 Hz, 1'-H), 8.15 (1H, s, 8-H).

Analysis Calculated for C$_{20}$H$_{33}$N$_5$O$_6$Si: C, 51.37; H, 7.11; N, 14.98. Found: C, 51.32; H, 7.14; N, 14.91.

5'-O-tert-Butyldimethylsilyl-N$^2$-isobutyryl-2, 3'-bis-O-[ (β-cyanoethylthio)thiocarbonyl]guanosine (24a)

To an ice-cooled solution of 23 (4.0 g, 8.56 mmol) and CS$_2$ (10 ml) in DMSO (20 ml) under nitrogen was added aqueous NaOH solution (50%) (7 mL, 87.5 mmol). After stirring for 35 min, β-bromopropionitrile ( 10 ml ) was added to the reaction mixture and the stirring was continued for an additional 1 h. The reaction mixture was diluted with ice-cold water and extracted with ethyl acetate. The organic layer was washed with water, dried (MgSO$_4$), and concentrated. Column chromatography over silica using CHCl$_3$-methanol (100:1) as the eluent yielded 5.5 g (88.6%) of 24a: mp 90°–92° C. dec; UV (methanol) λmax (pH 1) 277 nm, 256 (sh), 219 (sh); (pH 7) 277, 256 (sh), 219 (sh); (pH 11) 276 (sh); $^1$H NMR (DMSO-d$_6$) δ 0.10 (6H, s, (CH$_3$)$_2$Si), 0.90 (9H, s, (CH$_3$)$_3$CSi), 1.13 (6H, d, J =6.44 Hz, (CH$_3$)$_2$C), 2.55–3.10 (5H, m, CH$_2$CN and (CH$_3$)$_2$CH), 3.10–3.60 (4H, m, OCH$_2$), 3.95 (2H, m, 5'-H), 4 55 (1H, m, 4'-H), 6 20–6 60 (3H, m, 1',2', and 3' -H), 8.14 ( 1H, s, 8 -H).

Analysis Calculated for C$_{28}$H$_{39}$N$_7$O$_6$S$_4$Si: C, 46.32; H, 5.41; N, 13.50; S, 17.66. Found: C, 46.38; H, 5.43; N, 13.48; S, 17.73.

5'-O-tert-Butyldimethylsilyl-N$^2$-isobutyryl-2',3'-bis-O-[ (methylthio)-thiocarbonyl]guanosine (24b)

An aqueous NaOH solution (50%) (10 ml, 125 mmol) was added to an ice-cooled solution of 23 (8.0 g, 17.71 mmol) and CS$_2$ (15 ml) in DMSO (20 ml) under nitrogen. After stirring for 45 rain, CH$_3$I (20 ml) was added to the reaction mixture and the stirring was continued for an additional 1 h. The reaction mixture was diluted with ice-cold water and extracted with ethyl acetate. The organic layer was washed with water, dried (MgSO$_4$), and concentrated. Column chromatography over silica using CHCl$_3$-methanol (100:1) as the eluent yielded 9.5 g (86%) of 24b: mp 120°–122° C. dec; UV (methanol) λmax (pH 1) 280 nm, 258 (sh), 219 (sh); (pH 7) 279, 258 (sh), 219 (sh); (pH 11) 278 (sh); $^1$H NMR (DMSO-d$_6$) δ 0.01 (6H, s, (CH$_3$)$_2$Si), 0.90 (9H, s, (CH$_3$)$_3$CSi), 1.13 (6H, d, J= 6.74 Hz, (CH$_3$)$_2$C), 2.55 (3H, s, SCH$_3$), 2.65–2.80 (4 H, m, SCH$_3$ and (CH$_3$)$_2$CH), 3.99 (2H, m, 5'-H), 4.54 (1 H, m, 4'-H), 6.25–6.65 (3H, m, 1',2', and 3'-H), 8.14 (1H, s, 8-H).

Analysis Calculated for C$_{24}$H$_{37}$N$_5$O$_6$S$_4$Si: C, 44.49; H, 5.76; N, 10.81; S, 19.79. Found: C, 44.55; H, 5.77; N, 10.73; S, 19.74.

5'-O-tert-Butyldimethylsilyl-N$^2$-isobutyryl-2',3'-O-thionocarbonyl-guanosine (25)

A solution of 23 (1.5 g, 3.2 mmol) and thiocarbonyldiimidazole (1.1 g, 6 mmol) in DMF (15 ml) was heated at 75°–80° C. for 2 h. The solvent was removed under vacuum and the residue dissolved in CHCl$_3$. The organic layer was washed with water and dried (Na$_2$SO$_4$). Evaporation of CHCl$_3$ and subsequent purification of the residue by flash chromatography over silica fel using CHCl$_3$-methanol (100:2) as the eluent afforded 1.5 g (91%) of 25: mp 150°–155° C.; UV (methanol) λmax (pH 3) 280 nm, 258 (sh), 250 (sh), 243; (pH 7) 283,258 (sh), 250 (sh), 243; (pH 11) 265, 222; 1H NMR (DMSO-d$_6$) δ 0.0 (6H, s, (CH$_3$)$_2$Si), 0.77 (9H, s, (CH$_3$)$_3$CSi), 1.14 (6H, d, J=6.7 (CH$_3$)$_2$C), 2.75 (1H, septet, J=6.7 Hz, (CH$_3$)$_2$CH), 3.72 (2H, d, J=5.86 Hz, 5'-H), 4.40–4.60 (1H, m, 4'-H), 6.00 (1H, dd, J=2.6 Hz, 7.3 Hz, 3'-H), 6.21 (1H, dd, J=1 Hz, 7.3 Hz, 2'-H), 6.46 (1 H, d, J=1 Hz, 1'-H), 8.11 (1H, s, 8-H), 11.70 (1 H, br s, NH, exchangeable.)

Analysis Calculated for C$_{21}$H$_{31}$N$_5$O$_6$SSi: C, 49.49; H, 6.13; N, 13.74; S, 6.29. Found: C, 49.49; H, 6.18; N, 13:69; S, 6.20.

5'-O-tert-Butyldimethylsilyl-N$^2$-isobutyryl-2',3'-didehydro- 2',3'-dideoxyguanosine (26)

Method A: From 2',3'-O-bisdithiocarbonate 24a. A solution of tri-n-butyltin hydride (10.0 g, 34 mmol) and azobisisobutyronitrile (0.45 g) in benzene (20 ml) was added dropwise over one hour to a solution of 24a (4.5 g, 6.2 mmol) in dry benzene (30 ml), at 60°–65° C., under nitrogen. The reaction mixture was stirred at 60°–65° C. for 1 h. The solvent was removed under vacuum and the residue was partitioned between methanol and hexane. The methanol layer was separated, washed with hexane, and concentrated. The residue was purified by flash chromatography on a silica gel column using CHCl$_3$-methanol (100:2). Evaporation of the appropriate fractions yielded 1.5 g (55.8%) of the olefin 26 as a foam: mp 113°–115° C.; UV (methanol) λmax (pH 1) 260 nm; (pH 7) 282, 260; (pH 11) 270; $^1$H NMR (CDCl$_3$) δ 0.05 (6H, s, (CH$_3$)$_2$CSi), 1.11 (6H, d, J= 6.75 Hz, (CH$_3$)$_2$C), 2.77 (1H, septet, J=6.75 Hz, (CH$_3$)$_2$CH), 3.72 (2H, d, J=4.1 Hz, 5'-H), 4.89 (1H, m, 4'-H), 6.20 (1H, br d, J=5.86 Hz, 2'-H), 6.49 (1 H, br d, J=5.86 Hz, 3'-H), 6.76 (1H, m, 1'-H), 7.90 (1H, s, 8-H), 11.90 (1H, br s, NH, exchangeable).

Analysis Calculated for C$_{20}$H$_{31}$N$_5$O$_4$Si: C, 55.40; H, 7.21; N, 16.15. Found: C, 54.90; H, 7.25; N, 15.91.

Under similar conditions the bisxanthate 24b yielded 51.3% of 26.

Method B: From 2',3'-O-thionocarbonate 25. To a solution of 25 (1.0 g, 1.96 mmol) in THF (10 ml), cooled at 0° C., was added dropwise 1,3-dimethyl-2-phenyl- 1,3,2-diazaphospholidine (1.15 g, 5.9 mmol). The reaction mixture was stirred at room temperature for 3 h under nitrogen. The solvent was evaporated under vacuum and the residue was purified by chromatography on a silica gel column using CHCl$_3$-methanol (100:4). Evaporation of the appropriate fractions afforded 0.41 g (48%) of 26.

N$^2$-Isobutyryl-2',3'-didehydro-2',3'-dideoxyguanosine (27)

A 1M solution of tetra-n-butylammonium fluoride (4.3 ml, 4.3 mmol) in THF to an ice-cold solution of 26 (1.3 g, 3.0 mmol) in dry THF (30 ml) was added. The mixture was stirred at 0° C. for 30 min and then at room temperature for 2 h. The solvent was evaporated under reduced pressure and the residue was purified by chromatography on a silica gel column using a gradient of 5–15% methanol in CHCl$_3$ as the eluent. Concentration of the appropriate fractions yielded 0.8 grams (84%) of 27: mp >250° C. (benzenemethanol); $^1$H NMR (DMSO-d$_6$) δ 1.04 (6H, d, J=6.74 Hz, (CH$_3$)$_2$C), 2.75

(1H, septet, J=6.74 Hz, (CH$_3$)$_2$CH), 3.54 (2H, m, 5'-H), 4.85 (2H, m, 4'-H and OH, collapses to a multiplet integrating to one proton after D$_2$O exchange), 6.17 (1H, dt, J=1.47 Hz, 2.05 Hz, 6.0 Hz, 2'-H), 6.47 (1H, dt, J=1.47 Hz, 1.76 Hz, 5.0 Hz, 3'-H), 6.75 (1H, m, 1'-H), 7.99 (1H, s, 8-H), 11.90 (1H, br s, NH).

Analysis Calculated for C$_{14}$H$_{17}$N$_5$O$_4$.H$_2$O: C, 49.85; H, 5.68; N, 20.76. Found: C, 50.05; H, 5.71; N, 20.86.

N$^2$-Isobutyrl-2',3'-dideoxyguanosine (28)

A solution of 27 (0.3 g, 0.96 mmol) in methanol (50 ml) was hydrogenated under 30 psi of hydrogen gas with 10% Pd/C (50 rag). After one hour the reduction was incomplete. Additional catalyst (100 mg) was added to the reaction mixture and hydrogenation continued for an additional 5 hours. The catalyst was filtered off and the solvent was evaporated. The residue was purified by chromatography on a silica gel column using CHCl$_3$-methanol (10:1) as the eluent. Evaporation of the appropriate fractions yielded 0.2 g (66%) of 28 as a colorless solid: mp 245°–247° C. dec (benzene-methanol); $^1$H NMR (DMSO-d$_6$) δ 1.12 (6H, d, J =7.03 Hz, (CH$_3$)$_2$C), 1.85–2.15 (2H, m, 3'-H), 2.20– 2.52 (2H, m, 2'-H), 2.77 (1H, septet, J=7.03 Hz, (CH$_3$)$_2$CH), 3.55 (2H, m, 5'-H), 4.10 (1H, m, 4'-H), 4.94 (1H, t, J=4.7 Hz, OH, exchangeable), 6.08 (1 H, dd, J=1.46 Hz, 4.1 Hz, 1'-H), 8.26 (1H, s, 8-H), 11.88 (1H, br s, NH, exchangeable).

Analysis Calculated for C$_{14}$H$_{19}$N$_4$O$_4$.H$_2$O: C, 9.55; H, 6.24; N, 20.64. Found: C, 49.63; H, 6.27; N, 20.59.

2',3'-Didehydro-2',3'-dideoxyguanosine (9)

A solution of 27 (0.3 g, 0.94 mmol) in methanol saturated with ammonia (20 ml) was stirred at 50°–55° C. for 12 hours in a pressure vessel. The reaction mixture was cooled to room temperature. The solid obtained was filtered, washed with cold isopropanol, and dried. Crystallization from methanol afforded 0.2 g (81%) of 9 as an amorphous solid: mp >250° C.; UV (methanol) λmax (pH 1) 270 mn, 251; (pH 7) 269 (sh), 255; (pH 11) 268; 1H NMR (DMSO-d$_6$) 63.48–3.59 (2H, m, 5'-H), 4.70–5.00 (2H, m, 4'-H and OH), 6.08 (1H, br d, J=5.93 Hz, 2'-H), 6.40–6.47 (3H, m, 3'-H and NH$_2$), 6.68 (1H, m, 1'-H), 7.70 (1H, s, 8-H).

2',3'-Dideoxyguanosine (12)

A solution of 28 (0.2 g, 0.62 mmol) in methanolic ammonia (15 ml) was heated at 50°–55° C. in a pressure vessel for 12 hours. The reaction mixture was filtered and the filtrate was evaporated. Crystallization of the residue from methanol gave 0.15 g (96%) of 12 as a colorless solid: mp>250° C.; $^1$H NMR (DMSO-d$_6$) δ 1.95 (2H, m, 3'-H), 2.25 (2H, m, 2'-H), 3.53 (2H, m, 5'-H), 4.05 (1H, m, 4'-H), 4.90 (1H, t, J=4.7 Hz, OH, exchangeable), 5.98 (1H, dd, J=1.76 Hz, 4.1 Hz, 1'-H), 6.42 (2H, s, NH$_2$), 7.93 (1H, s, 8-H), 10.55 (1H, s, NH, exchangeable).

Preparation of 2',3'-Dideoxydidehydrocytidine

The preparation of 2',3'-unsaturated nucleosides via their bisxanthates was also extended to cytidine to give a fair yield of 2',3'-dideoxydidehydrocytidine 32 (Scheme 4). However, in the case of cytidine the thionocarbonate method was not successful due to the instability of 31. The following working example further illustrates the method of the present invention to produce 2',3'-dideoxydidehydrocytidine.

4-Acetyl-5'-O-tert-butyldimethylsilyl-2, 3'-bis-O-[ (methylthio)-thiocarbonyl]cytidine (30)

N$^4$-acetylcytidine (8.35 g, 29.3 mmol), imidazole (5.0 g, 73.53 mmol) and tert-butyldimethylsilyl chloride (5.75 g, 38.2 mmol) were stirred in dry DMF (50 ml) for 5 hours. The solvent was removed in vacuo and the oily residue was dissolved in CHCl$_3$ (100 ml), washed with water, dried (Na$_2$SO$_4$), and concentrated. The resulting syrupy residue was purified by flash vacuum chromatography on a silica gel column using gradient of 0–5% methanol in CHCl$_3$. The solvent from the combined fractions was evaporated to give 8.15 g (70%) of 5'-O-t-butyldimethylsilyl protected cytidine as a white foamy solid: mp 159–161° C.; UV (methanol) λmax (pH 1) 300 nm, 246; (pH 7) 298, 246; (pH 11) 272, 231 (sh); $^1$H NMR (DMSO-d$_6$) δ 0.09 (6H, s, (CH$_3$)$_2$Si), 0.90 (9H, s, (CH$_3$)$_3$CSi); 2.09 (3H, s, CH$_3$), 3.70–4.10 (5 H, m, 2', 3', 4', and 5'-H), 5.05 (1H, br s, OH), 5.55 (1H, d, J=4.7 Hz, OH), 5.77 (1H, m, 1'-H), 7.19 (1H, d, J=7.6 Hz, 5-H), 8.31 (1H, d, J=7.6 Hz, 6-H), 10.86 (1H, s, NH).

Analysis Calculated for C$_{17}$H$_{29}$N$_3$O$_6$Si: C, 51.11; H, 7.32; N, 10.52. Found: C, 50.94; H, 7.32; N, 10.46.

A solution of N$^4$-acetyl-5'-O-tert-butyldimethylsilylcytidine (8.15 g, 20.4 mmol) prepared as above and imidazole (300 mg) in dry THF (50 ml) was cooled to 5°–10° C. and flushed with nitrogen. NaH (60% dispersion, 3.3 g, 82.5 mmol) was added to the reaction mixture portionwise over 5 minutes. After 1 hour of stirring, the mixture was treated with CS$_2$ (8.4 g, 110.5 mmol) and stirred for an additional 30 minutes. CH$_3$I (12.0 g, 85 mmol) was added to the reaction mixture and then the stirring was continued for an additional 30 minutes. The reaction mixture was diluted with diethyl ether (250 ml), washed with ice-cold water (2×50 ml), and dried over Na$_2$SO$_4$. The organic layer was concentrated and the resulting yellow oily residue was purified by flash chromatography over silica using CHCl$_3$-ethyl acetate (10:1) as the eluent to yield 6.0 g (51%) of 30: mp 161°–163° C. (benzene-hexane); UV (methanol) λmax (pH 1) 280 nm, 247; (pH 7) 279, 247: (pH 11) 277, 224 (sh); $^1$H NMR (DMSO-d$_6$) δ 0.04 (6H, s, ((CH$_3$)$_2$Si), 0.83 (9H, s, (CH$_3$)$_3$CSi), 2.06 (3H, s, COCH$_3$), 2.53 (3H, s, SCH$_3$), 2.56 (3H, s, SCH$_3$), 3.91 (2H, M, 5'-H), 4.50 (1H, m, 4'-H), 6.10–6.40 (3H, m, 1',2', and 3'-H), 7.19 (1H, d, J=7.6 Hz, 5-H), 8.13 (1H, d, J=7.6 Hz, 6-H), 10.91 (1H, s, NH).

Analysis Calculated for C$_{21}$H$_{33}$N$_3$O$_6$S$_4$Si: C, 43.50; H, 5.74; N, 7.25; S, 22.12. Found: C, 43.60; H, 5.76; N, 7.22; S, 22.20.

N$^4$-Acetyl-5'-O-tert-butyldimethylsilyl-2',3'-didehydro-2',3'-dideoxycytidine (32)

Tri-n-butyltin hydride (12.0 g, 41 mmol) in toluene (20 ml) was added dropwise over one hour to a refluxing solution of 30 (4.0 g, 6.91 mmol) and azobisisobutyronitrile (500 mg) in dry toluene (30 ml) under nitrogen. The reaction mixture was refluxed for 2 h. The solvent was then removed under vacuum and the oily residue was partitioned between methanol and hexane. The methanol layer was separated and washed with hexane. The solvent was removed in vacuo and the syrupy residue was purified by chromatography over silica using CHCl$_3$-methanol (100:2.5) to yield 1.5 g (59%) of 32: mp 168°–170° C. (softens); UV (methanol) λmax (pH 1) 301 nm, 242; (pH 7) 297, 246; (pH 11) 269; $^1$H NMR (DMSO-d$_6$) δ 0.04 (6H, s, (CH$_3$)$_2$Si), 0.85 (9H, s, (CH$_3$)$_3$CSi), 2.09 (3H, s, COCH$_3$), 3.82 (2H, d, J= 3.22 Hz, 5'-H), 4.90 (1H, m, 4'-H), 6.03 (1H, br d, J=6.15 Hz, 2'-H), 6.38 (1H, br d, J=6.15 Hz, 3'-H), 6.88 (1H, m, 1'-H), 7.17

(1H, d, J=7.3 Hz, 5H), 8.11 (1H, d, J=7.3 Hz, 6-H), 10.88 (1H, s, NH).

Analysis Calculated for $C_{17}H_{27}N_3O_4Si$: C, 55.86; H, 7.45; N, 11.50. Found: C, 55.76; H, 7.50; N, 11.49.

$N^4$-Acetyl-2',3'-didehydro-2',3'-dideoxycytidine (33)

A solution of 32 (1.5 g, 4.1 mmol) in THF (30 ml) and 5 ml (5.0 mmol) of a 1M solution of tetra-n-butylammonium fluoride solution in THF were stirred in an ice-bath for 10 minutes and then at room temperature for 1 hour. The solvent was removed in vacuo. The resulting residue was purified by chromatography using 5% methanol in $CHCl_3$ to obtain 0.88 g (85%) of 33 as colorless solid: mp 180°–182° C. dec (benzene-methanol); $^1H$ NMR (DMSO-$d_6$) 6 2.09 (3H, s, $COCH_3$), 3.63 (2H, m, 5'-H), 4.85 (1H, m, 4'-H), 4.99 (1H, t, J=5.27 Hz, OH), 5.95 (1H, br d, J=5.8 Hz, 2'-H), 6.40 (1H, br d, J=5.8 Hz, 3'-H), 6.87 (1H, m, 1'-H), 7.15 (1H, d, J=7.3 Hz, 5-H), 8.20 (1H, d, J=7.3 Hz, 6-H), 10.86 (1H, s, NH).

Analysis Calculated for $C_{11}H_{13}N_3O_4$: C, 52.59; H, 5.22; N, 16.72 Found: C, 52.48; H, 5.24; N, 16.68.

2',3'-Didehydro-2',3'-dideoxycytidine (3)

A solution of 33 (0.26 g, 1.03 mmol) in methanol saturated with ammonia (20 ml) was stirred at 45°–50° C. for 12 hours. The solvent was removed under reduced pressure. The residue was triturated with isopropanol, filtered, and then washed with isopropanol to yield 0.15 g (69%) of 3: mp 167°–169° C. (benzene-methanol) (Lit. mp 168°– 169° C.); $^1H$ NMR (DMSO-$d_6$) δ 3.51 (2H, m, 5'-H), 4.75 (1H, m, 4'OH), 4.85 (1H, t, J=5.5 Hz, OH), 5.68 (1 H, d, J=7.3 Hz, 5-H), 5.85 (1H, br d, J=5.9 Hz, 2'-H), 6.35 (1H, br d, J=5.9 Hz, 3'-H), 6.89 (1H, m, 1'-H), 7.10 (2H, s, $NH_2$), 7.67 (1H, d, J=7.3 Hz, 6-H).

$N^4$-Acetyl-2',3'-dideoxycytidine (34)

A solution of 33 (0.78 g, 3.1 mmol) in ethanol (100 mL) was hydrogenated under 15 psi of hydrogen gas in the presence of 10% Pd/C (0.15 g) for 12 hours. The reaction mixture was filtered, concentrated, and the residue was purified by chromatography over silica using 5% methanol in $CHCl_3$ as the eluent to obtain 0.61 g (77.5%) of 34 as a colorless solid: mp 143°– 145° C. (benzene-methanol); $^1H$ NMR (DMSO-$d_6$) δ 1.60–2.50 (7H, m, 2',3'-H and $COCH_3$), 3.40–3.85 (2H, m, 5'-H), 3.90–4.30 (1H, m, 4'-H), 5.07 (1H, t, J=5.0 Hz, OH), 5.91 (1H, m, 1'-H), 7.17 (1H, d, J=7.6 Hz, 5-H), 8.32 (1H, d, J=7.3 Hz, 6-H), 10.80 (1H, s, NH).

Analysis Calculated for $C_{11}H_{15}N_3O_4$: C, 52.17; H, 5.97; N, 16.59. Found: C, 52.07; H, 6.00; N, 16.53.

2',3'-Dideoxycytidine (4)

A solution of 34 (0 6 g, 2.4 mmol ) in methanol saturated with ammonia ( 20 ml ) was stirred at 50° C. for 12 hours in a pressure vessel. The reaction mixture was concentrated and the residue was triturated with isopropanol, filtered, and dried to yield 0.4 g (80%) of 4: mp 207°–209° C. (benzene-ethanol); $^1H$ NMR (DMSO-$d_6$) δ 1.50–2.50 (4H, m, 2' and 3'-H), 3.63 (2H, m, 5'-H), 4.00 (1H, m, 4'-H), 4.96 (1H, t, J=4.9 Hz, OH), 5.69 (1H, d, J=7.25 Hz, 5-H), 5.95 (1H, m, 1'-H), 7.05 (2H, s, $NH_2$), 7.89 (1 H, d, J=7.3 Hz, 6-H).

Preparation of 2',3'-Didehydrodideoxyuridine

Figure 6:
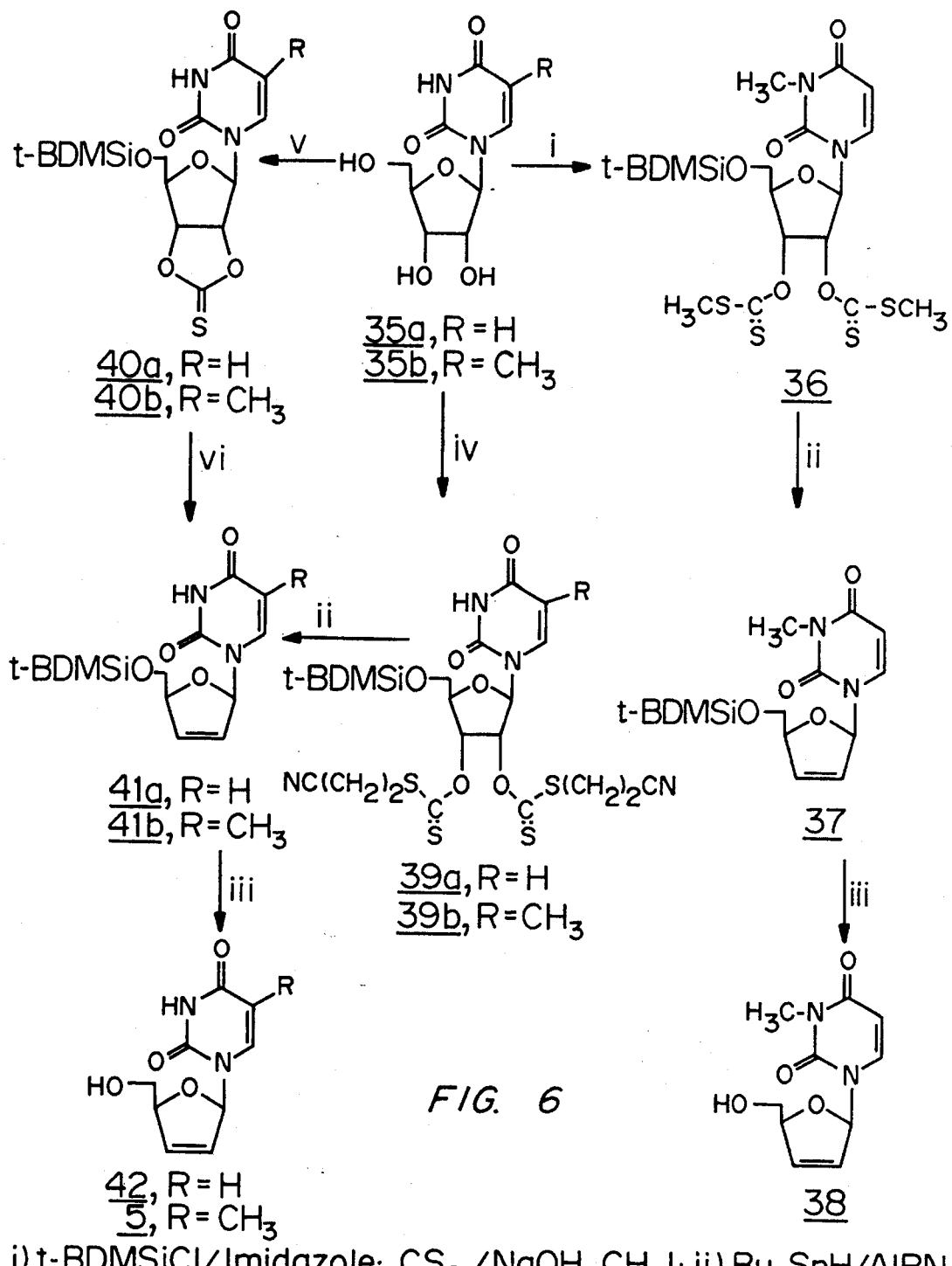
FIG. 6 is an illustration of Scheme 5 according to the present invention for the synthesis of 2',3'-dideoxyuridine and 2',3'-dideoxy-1-(β-Dribofuranosyl)thymidine.

Both the thionocarbonate and bisxanthate methods were also applied to uridine (35a) and 1-(β-Dribofuranosyl)thymine (35b) (Scheme 5, FIG. 6). β-Bromopropionitrile was used instead of methyl iodide as the alkylating agent in order to avoid $N^3$-alkylation. The following working example further illustrates the preparation of 2',3'-didehydrodideoxyuridine by the method of the present invention.

5'-O-tert-Butyldimethylsilyl-2',3'-didehydro-2',3'-ideoxy-$N^3$-methyluridine (37)

To a solution of 5'-O-tert-butyldimethylsilyluridine (3.21 g, 8.97 mmol) and $CS_2$ (8 ml) in DMSO (12 ml), cooled to 15° C. under nitrogen was added 8 ml of a 5N aqueous NaOH solution. After stirring for 20 min, $CH_3I$ (14 ml) was added to the mixture and stirring was continued for an additional 45 min. TLC of the reaction mixture showed 3 products; the main product at Rf 0.78, traces of a product at Rf 0.46 and a yellow product moving with the solvent front (benzene-ethyl acetate, 4:1). The reaction mixture was diluted with ice-water and extracted with ethyl acetate. The organic layer was dried over $Na_2SO_4$ and evaporated to give 36 as a yellow oil which was used in the next reaction without purification. A small amount of the product was purified by preparative TLC; $^1H$ NMR (DMSO-$d_6$) δ 0.0 (6H, s, $(CH_3)_2Si$), 0.80 (9H, s, $(CH_3)_3CSi$), 2.47 (3 H, s, $SCH_3$), 2.52 (3H, s, $SCH_3$), 3.05 (3H, s, N-$CH_3$), 3.82 (2H, d, J=2.9 Hz, 5'-H), 4.38 (1H, m, 4'-H), 5.73 (1H, d, J=7.5 Hz, 5-H), 6.12 (3H, m, 1', 2', and 3'-H), 7.72 (1H, d, J=7.5 Hz, 6-H). To a refluxing solution of the 2',3'-O-dithiocarbonate 36 in toluene (30 ml) under nitrogen was added dropwise a solution of tri-n-butyltin hydride (11.0 g, 37.9 mmol) and azobisisobutyronitrile (0.68 g, 4.1 mmol) in toluene (30 ml). The reaction mixture was refluxed for 1 hour and cooled. Evaporation of the solvent and purification of the residue by chromatography on a silica gel column using benzene-ethyl acetate (7:1) as the eluent yielded 1.85 g (63.6%) of the olefin 37: mp 116°–117° C. (diethyl ether-hexanes); $^1H$ NMR (DMSOd $_6$) δ 0.0 (6H, s, $(CH_3)_2Si$), 0.82 (9H, s, $(CH_3)_3CSi$), 3.13 (3H, s, $NCH_3$), 3.76 (2H, d, J=3.2 Hz, 5'-H), 4.80 (1H, m, 4'-H), 5.62 (1H, d, J=7.9 Hz, 5-H), 5.92 (1H, dt, J=1.4 Hz, 2.1 Hz, 6.2 Hz, 2'-H), 6.37 (1H, dt, J=6.0 Hz and 1.6 Hz each, 3'-H), 6.82 (1H, quintette J=1.4 Hz, 1.7 Hz, 3.2 Hz, 1'-H), 7.65 (1H, d, J=7.9 Hz, 6-H).

Analysis Calculated for $C_{16}H_{26}N_2O_4Si$: C, 56.77; H, 7.74; N, 8.27. Found: C, 56.77; H, 7.81; N, 8.22.

2',3'-Didehydro-2',3'-dideoxy-$N^3$-methyluridine (38)

A solution of 37 (1.8 g, 5.3 mmol) in THF (10 ml) and 1M solution of tetra-n-butylammonium fluoride (6.5 ml, 65 mmol) in THF were stirred at 0° C. for 20 min. The solvent was evaporated and the residue was purified chromatographically using $CHCl_3$-methanol (25:0.5) as the eluent to obtain 1.05 g (88%) of 38: mp 203–204° C. (methanol); $^1H$ NMR ( DMSO-$d_6$ ) δ 3.15 ( 3H, s, $NCH_3$ ), 3.58 (2H, dd, J=3.5 hz, 5.3 Hz, 5'-H), 4.79 (1H, m, 4'-H), 4.93 (1H, t, J=5.3 Hz, OH), 5.71 (1H, d, J=8.3 Hz, 5-H), 5.92 (1H, dt, J=1.7 Hz, 2.6 Hz, 7.3 Hz, 2'-H), 6.37 (1H, dt, J=7.1 HZ and 2.1 Hz each, 3'-H), 6.86 (1H, quintette, J=1.8 Hz, 1.9 Hz, 3.9 Hz, 1'-H), 7.78 (1H, d, J=8.1 Hz, 6-H); $^{13}C$ NMR (DMSO-$d_6$) δ 161.7, C-4; 150.8, C-2; 138.7, C-6; 134.6, 125.2, C-2' and C-3'; 100.1, C-5; 90.1, 87.1, C-1', C-4'; 62.1, C-5'; 26.6, $CH_3$.

Analysis Calculated for $C_{10}H_{12}N_2O_4$: C, 53.57; H, 5.39; N, 12.49. Found: C, 53.58; H, 5.39; N, 12.44.

5'-O-tert-Butyldimethylsilyl-2',3'-bis-O-[(β-cyano-ethylthio)thiocarbonyl] -uridine (39a)

5'-O-tert-Butyldimethylsilyluridine (0.5 g, 1.4 mmol) was reacted with $CS_2$ (1.5 ml in 4mL of DMSO) and two equivalents of NaOH (5N solution), and then alkylated with β-bromopropionitrile (3.9 mL) according to the procedure described for 36. Purification by chromatography using $CHCl_3$-methanol (60:1) as the eluent yielded 0.77 g (89.5%) of 39a. The product could not be analyzed due to its instability; $^1$H NMR δ 0.0 (6H, s, $(CH_3)_2Si$), 0.80 (9H, s, $(CH_3)_3CSi$), 2.67–3.49 (8H, m, $CH_2CH_2CN$), 3.82 (2H, unresolved, 5'-H), 4.44 (1H, d, J=2.1 Hz, 4'-H), 5.62 (1H, dd, J=1.2 Hz, 8.2 Hz, 5-H), 5.93–6.22 (3H, m, 1', 2', and 3'-H), 7.64 (1H, d, J=8.2 Hz, 6-H), 11.37 (1H, d, J=1.2 Hz, NH).

5'-O-tert-Butyldimethylsilyl-2',3'-bis-O-[(β-cyano-ethylthio)thiocarbonyl] -5-methyluridine (39b)

A solution of 5-methyluridine (1.42 g, 5.49 mmol), imidazole (0,816 g, 11.26 mmol) and tertbutyldimethylsilyl chloride (0.9 g, 6.01 mmol) was stirred at room temperature for 24 hours and then concentrated in vacuo. The residue obtained was purified by chromatography on a silica gel column using $CHCl_3$-methanol (30:1) as the eluent to give 1.49 g (73%) of 5'-O-tert-butyldimethylsilyl-5-methyluridine as a colorless solid: mp 209°–211° C. (ethyl acetate); $^1$H NMR (DMSO-$d_6$) δ 0.0 (6H, s, $(CH_3)_2Si$), 0.81 (9H, s, $(CH_3)_3CSi$), 3.60–3.90 (5H, m, 2, 3, 4' and 5'-H), 4.97 (1H, d, J=4.39 Hz, 3'-OH, exchangeable), 5.25 (1H, d, J=5.57 Hz, 2'-OH, exchangeable), 5.71 (1H, d, J=5.57 Hz, 1'-H), 7.32 (1H, s, 6-H), 11.21 (1H, s, NH, exchangeable).

Analysis Calculated for $C_{16}H_{28}N_2O_6Si$: C, 51.58; H, 7.57; N, 7.52. Found: C, 51.61; H, 7.59; N, 7.48.

5'-O-tert-Butyldimethylsilyl-5-methyluridine (0.372 g, 1.0 mmol) was reacted with $CS_2$ (2.5 g, 33.15 mmol) in the presence of 5N aqueous NaOH (3.5 ml) in DMSO (3.5 ml) and alkylated with β-bromopropionitrile (4.0 g, 30.35 mmol) according to the procedure described for 36. Purification by chromatography on a silica gel column using $CHCl_3$-methanol (50:1) as the eluent yielded 0.6 g (95%) of 39b as a pale yellow glassy solid: IR (KBr) 2250 (C≡N), 1760–1650 (C=O) cm$^{-1}$; $^1$H NMR δ 0.18 (6H, s, $(CH_3)_2Si$), 0.97 (9H, s, $(CH_3)_3CSi$), 1.94 (3H, d, J=1.17 Hz, 5-$CH_3$), 2.85 (4 H, t, J=7.0 Hz, 2×$CH_2CN$), 3.35 (2H, t, J=7.0 Hz, S-$CH_2$), 3.45 (2H, t, J=7.0 Hz, S-$CH_2$), 3.98 (2 H, m, 5'-H), 4.43 (1H, d, J=1.47 Hz, 4'-H), 5.98 (1 H, dd, J=5.56 Hz, 7.62 Hz, 2'-H), 6.32 (1H, dd J= 1.47 Hz, 5.56 Hz, 3'-H), 6.52 (1H, d, J=7.62 Hz, 1'-H), 7.48 (1H, d, J=1.17 Hz, 6-H).

5'-O-tert-Butyldimethylsilyl-2',3'-O-thionocarbonyl-uridine (40a)

A solution of 5'-O-tertbutyldimethylsilyluridine (1.59 g, 4.4 mmol) and thiocarbonyldiimidazole (1.22 g, 6.85 mmol) in DMF (5 ml) was stirred at room temperature overnight. The solvent was evaporated under reduced pressure and the residue was dissolved in $CHCl_3$. The organic layer was washed with water, dried over $Na_2SO_4$, and concentrated. Trituration of the residue with ethanol afforded a crystalline mass which was purified by flash chromatography using hexane:acetone (3: 1) as the eluent. Yield 0.85 g (48%) of 40a: mp 172°–176° C.; UV (methanol) λmax (pH$_3$) 239; (pH 7) 240; (pH 11) 232, 257 (sh); $^1$H NMR (DMSO-$d_6$) δ 0.03 (6H, s, $(CH_3)_2Si$), 0.85 (9H, s, $(CH_3)_3CSi$), 3.81 (2H, d, J=5.86 Hz, 5'-H), 4.30–4.50 (1H, m, 4'-H), 5.48–5.68 (2H, m, 2' and 3'-H), 5.90–6.00 (2H, m, 1' and 5-H), 7.72 (1H, d, J=7.96 Hz, 6-H), 11.50 (1H, s, NH).

Analysis Calculated for $C_{16}H_{24}N_2O_6SSi$: C, 47.98; H, 6.04; N, 6.99; S, 8.00. Found: C, 48.08; H, 6.08; N, 6.97; S, 8.04.

5'-O-tert-Butyldimethylsilyl-5-methyl-2',3'-Othionocarbonyluridine (40b)

A solution of 5'-O-tertbutyldimethylsilyl- 5-methyluridine (40b) (0.372 g, 1.0 mmol) in THF (6 ml) was stirred with thiocarbonyldiimidazole (0.22 g, 1.2 mmol) under nitrogen at room temperature for 24 h. The solvent was removed under vacuum and the residue was purified by flash chromatography using $CHCl_3$-methanol (50:1) as the eluent to obtain 0.28 g (67%) of 40b as a glassy material: $^1$H NMR (DMSO-$d_6$) δ 0.075 (6H, s, $(CH_3)_2Si$), 0.89 (9H, s, $(CH_3)_3CSi$), 1.94 (3H, s, 5-$CH_3$), 3.84 (2H, d, J=5.57 Hz, 5'-H); 4.40 (1H, m, 4'-H); 5.50 (1H, m, 2'-H); 5.70 (2H, m, 1' and 3'-H); 7.11 (1H, s, 6-H), 9.19 (1H, s, NH, exchangeable).

Analysis Calculated for $C_{17}H_{26}N_2O_6SSi$: C, 49.25; H, 6.32; N, 6.75; S, 7.73. Found: C, 49.07; H, 6.37; N, 6.71; S, 7.65.

5'-O-tert-Butyldimethylsilyl-2',3'-didehydro-2',3'-dideoxyuridine (41a)

Method A: From 2',3'-bis-O-dithiocarbonate 39a. To a refluxing solution of 39a (0.50 g, 0.81 mmol) in toluene (30 ml) under nitrogen was added to a solution of tri-n-butyltin hydride (1.74 g, 6.48 mmol) and azobisisobutyronitrile (0.27 g, 1.65 mmol) in toluene (25 ml) dropwise over a 15 minute period. The mixture was refluxed for 45 min, cooled, and the solvent was evaporated. The residue was purified by column chromatography using benzene-ethyl acetate (13:7) as the eluent to give 0.23 g (87%) of 41a: mp 167°–168° C. (diethyl ether-hexanes); $^1$H NMR (DMSO-$d_6$) δ 0.0 (6H, s, $(CH_3)_2Si$), 0.80 (9H, s, $(CH_3)_3CSi$), 3.75 (2H, d, J=3.3 Hz, 5'-H), 4.78 (1 H, m, 4'-H), 5.48 (1H, d, J=8.1 Hz, 5-H), 5.90 (1 H, dt, J=6.0 Hz, 1.7 Hz, 2'-H); 6.35 (1H, dt, J= 5.8 Hz and 1.5 Hz, 3'-H), 6.77 (1H, m, 1'-H), 7.60 (1 H, d, J=8.1 Hz, 6-H); 11.3 (1H, br s, NH).

Analysis Calculated for $C_{15}H_{24}N_2O_4Si$: C, 55.53; H, 7.45; N, 8.63. Found: C, 55.63; H, 7.48; N, 8.61.

Method B: From 2',3'-O-thionocarbonate 40a. A solution of 40a (0.345 g, 0.85 mmol) in triethyl phosphite (15 ml) was heated at reflux under nitrogen for 4 hours. Excess triethyl phosphite was then removed under vacuum. The residual oil was dissolved in $CHCl_3$, washed with water, and dried over $Na_2SO_4$. Evaporation of $CHCl_3$ and purification of the residue by flash chromatography over silica gel using benzene-ethyl acetate (13:7) afforded 0.17 g (62%) of 41a.

5'-O-tert-Butyldimethylsilyl-5-methyl-2',3'-didehydro-2',3'-dideoxy-uridine (41b)

Method A: From 2',3'-bis-O-dithiocarbonate 39b. A solution of tri-n-butyltin hydride (1.5 g, 5.4 mmol) in toluene (2 ml) was added dropwise to a solution of 39b (0.6 g, 0.95 mmol) and azobisisobutyronitrile (15 mg) in dry toluene (15 ml) under nitrogen at 60° C. The reaction mixture was stirred at 90° C. for 30 minutes. The solvent was removed under vacuum. The residue was dissolved in acetonitrile (20 ml) and washed with hexane (2×10 ml). Evaporation of acetonitrile under vacuum gave a solid, which was purified by flash chromatography using $CHCl_3$-methanol (30:1) as the eluent to obtain 0.208 g (65%) of 41b as colorless powder: mp 169°–171° C.; UV (methanol) λmax 265 nm;

$^1$H NMR (DMSO-d$_6$) δ 0.08 (6H, s, (CH$_3$)$_2$Si), 0.90 (9H, s, (CH$_3$)$_3$CSi), 1.90 (3H, d, J=1.17 Hz), 3.85 (2H, d, J=3.8 Hz, 5'-H), 4.82 (1H, m, 4'-H), 5.80 (1H, br d, J=6.2 Hz, 2'-H), 6.25 (1H, br d, J=6.2H, 3'-H), 6.95 (1H, m, 1'-H), 7.33 (1H, d, J=1.17 Hz, 6H); 8.53 (1H, br s, NH, exchangeable).

Analysis Calculated for C$_{16}$H$_{26}$N$_2$O$_4$Si: C, 56.73; H, 7.74; N, 8.27. Found C, 56.69; H, 7.82; N, 8.23.

Method B: From 2',3'-O-thionocarbonate 40b. A solution of 40b (55 mg, 0.15 mmol) and 1,3-dimethyl- 2-phenyl-1,3,2-diazaphospholidine (0.4 ml) in THF (2 ml) was stirred under nitrogen for 24 hours. The solvent was removed under reduced pressure. The residue was purified by chromatography using CHCl$_3$-methanol (50:1) as the eluent to obtain 24 mg (52%) of 4lb.

2',3'-Didehydro-2',3'-dideoxyuridine (45)

A solution of 41a (0.38 g, 1.17 mmol) in THF (10 ml) was stirred with a 1M solution of tetra-n-butylammonium fluoride (1.5 ml, 1.5 mmol) in THF for 2 hours. The solvent was evaporated and the residue was purified by chromatography on a silica gel column using CHCl$_3$-methanol (20:1) as the eluent to obtain 0.164 g (67%) of 42: mp 153°–155° C. (methanol); 13C NMR (DMSO-d$_6$) δ 162.7, C-4; 150.4, C-2; 140.3, C-6; 134.6, 125.2, C-2' and C-3'; 101.1, C-5; 89.1, C-1'; 87.0, C-4'; 62.2, C- 5'.

2',3'-Didehydro-2',3'-dideoxy-5-methyluridine (5)

A solution of 41b (80 mg. 0.23 mmol) in THF (10 ml) was stirred with a 1M solution of tetra-n-butyl-ammonium flouride in THF (0.3 mL, 0.3 mmol) at room temperature for 2 h. The solvent was removed under vacuum and the residue was purified by chromatography using CHCl$_3$-methanol (30:1) as the eluent to obtain 41 mg (80%) of as colorless solid: mp 164° C.; $^1$H NMR (DMSO-d$_6$) δ 1.90 (3H, d, J=1.17 Hz, 5-CH$_3$), 3.62 (2H, dd, J= 3.52 Hz, 4.98 Hz, 5'-H), 4.75 (1H, m, 4'-H); 4.95 (1H, t, J=4.98 Hz, 5'-OH, exchangeable), 5.85 (1H, br d, J=6.2 Hz, 2'-H), 6.40 (1H, br d, J=6.2 Hz, 3'H), 6.80 (1H, m, 1'-H), 7.62 (1H, d, J=1.17 Hz, 6H), 11.25 (1H, s, NH, exchangeable).

Modifications and variations of the present invention for a general method of preparation of 2',3'-didehydrodideoxy and 2',3'-dideoxy nucleusides will be obvious to those skilled in the art from the foregoing detailed description of the invention. Such modifications and variations are intended to come within the scope of the appended claims.

I claim:

1. A process for preparing 2',3'-didehydro- 2',3'-dideoxynucleosides comprising:

preparing a nucleoside of the structure

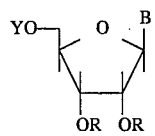

by reacting a 5'-hydroxy protected nucleoside with carbon disulfide and an alkyl or substituted alkyl halide in base; wherein B is a heterocycle selected from the group consisting of a purine and a pyrimidine, Y is an oxygen protecting group, each R is C(S)SR', where R' is an alkyl or cyanoalkyl group of C$_1$ to C$_{15}$; and deoxygenating the nucleoside to the corresponding 2',3'-didehydrodideoxynucleoside.

2. The process of claim 1 wherein R is selected from the group consisting of C(S)SCH$_3$ and C(S)SCH$_2$CH$_2$CN.

3. The process of claim 1 wherein Y is t-butyl dimethylsilyl.

4. A process for preparing a 2',3'-dideoxynucleoside comprising:

preparing a nucleoside of the structure

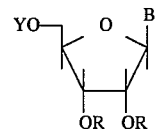

by reacting a 5'-hydroxy protected nucleoside with carbon disulfide and an alkyl or substituted alkyl halide in base; wherein B is a heterocycle selected from the group consisting of a purine, and a pyrimidine, Y is an oxygen protecting group, each R is C(S)SR', where R' is an alkyl or cyanoalkyl group of C$_1$ to C$_{15}$;

deoxygenating the nucleoside to the corresponding 2',3'-didehydro-2',3'-dideoxynucleoside; and reducing the 2',3'-didehydrodideoxynucleoside to the corresponding 2',3'-dideoxynucleoside.

5. The process of claim 4 further comprising removing the oxygen protecting group before reducing the 2',3'-didehydrodideoxynucleoside.

6. The process of claim 5 further comprising removing the oxygen protecting group with tributyl ammonium fluoride.

7. The process of claim 4 wherein the 2',3'-didehydro-2',3'-dideoxynucleoside nucleoside is reduced in hydrogen gas with palladium on carbon.

8. The process of claim 1 wherein amino groups on the heterocycle are protected before deoxygenation.

9. The process of claim 8 wherein the amino groups are protected with acyl groups.

10. The process of claim 9 further comprising removing the acyl protecting group from the amino group of the organic base of the nucleoside with methanolic ammonia.

11. The process of claim 1 wherein B is adenine.

12. The process of claim 1 wherein B is hypoxanthine.

13. The process of claim 12 wherein R is C(S)SCH$_2$CH$_2$CN.

14. The process of claim 1 wherein B is guanine.

15. The process of claim 1 wherein B is uracil.

16. The process of claim 15 wherein R is C(S)SCH$_2$CH$_2$CN.

17. The process of claim 1 wherein B is cytosine.

18. The process of claim 1 wherein the base is thymine.

19. A process for preparing 2',3'-didehydrodideoxynucleosides comprising mildly deoxygenating a nucleoside of the structure

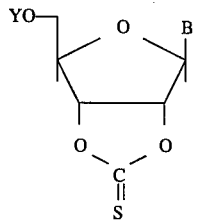

wherein B is selected from the group consisting of a purine, pyrimidine, and Y is an oxygen protecting group, wherein the deoxygenating agent is 1,3-dimethyl-2-phenyl- 1,3,2-diazaphosphilidine.

20. The process of claim 19 wherein Y is t-butyl dimethylsilyl.

21. A process for preparing 2',3'-dideoxynucleosides comprising mildly deoxygenating a nucleoside of the structure

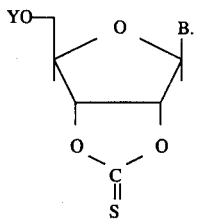

wherein B is selected from the group consisting of a purine, pyrimidine, and Y is an oxygen protecting group, wherein the deoxygenating agent is 1,3-dimethylphenyl-1,3,2-diazaphosphilidine; and then reducing the 2',3'-didehydrodideoxynucleoside to the corresponding 2',3-dideoxynucleoside.

22. The process of claim 19 further comprising removing the oxygen protecting group before reducing the 2',3'-didehydrodideoxynucleoside.

23. The process of claim 22 further comprising removing the oxygen protecting group with tributyl ammonium flouride.

24. The process of claim 21 wherein the 2',3'-didehydrodideoxynucleoside is reduced in hydrogen gas with palladium on carbon.

25. The process of claim 19 wherein amino groups on the heterocycle are protected before deoxygenation.

26. The process of claim 25 wherein the amino groups are protected with acyl groups.

27. The process of claim 26, further comprising removing the acyl protecting group from the amino group of the organic base of the nucleoside with methanolic ammonia.

28. The process of claim 19, wherein B is selected from the group consisting of adenine, hypoxanthine, guanine, uracil, cytosine, and thymine.

* * * * *